US007923030B2

(12) United States Patent
Lapidot et al.

(10) Patent No.: US 7,923,030 B2
(45) Date of Patent: Apr. 12, 2011

(54) AGENT-ENCAPSULATING MICRO- AND NANOPARTICLES, METHODS FOR PREPARATION OF SAME AND PRODUCTS CONTAINING SAME

(75) Inventors: Noa Lapidot, Mavasseret Zion (IL); Merav Blanca, Modiin (IL); Claudio Rottman, Modiin (IL); Oleg Naigertsik, Haifa (IL)

(73) Assignee: Sol-Gel Technologies, Inc., Ness Ziona (IL)

( * ) Notice: Subject to any disclaimer, the term of this patent is extended or adjusted under 35 U.S.C. 154(b) by 1427 days.

(21) Appl. No.: 10/549,148

(22) PCT Filed: Mar. 11, 2004

(86) PCT No.: PCT/IL2004/000236
§ 371 (c)(1),
(2), (4) Date: Sep. 13, 2005

(87) PCT Pub. No.: WO2004/081222
PCT Pub. Date: Sep. 23, 2004

(65) Prior Publication Data
US 2006/0251687 A1 Nov. 9, 2006

Related U.S. Application Data

(60) Provisional application No. 60/454,303, filed on Mar. 14, 2003.

(51) Int. Cl.
*A61K 9/00* (2006.01)
*A61K 9/14* (2006.01)
*A61K 6/00* (2006.01)
*A61K 8/00* (2006.01)
*A61K 8/11* (2006.01)
*A61K 8/18* (2006.01)
*A61K 8/19* (2006.01)
*A61K 8/25* (2006.01)
*A61K 8/26* (2006.01)
*A61K 8/29* (2006.01)
*A61K 47/00* (2006.01)
*A61K 47/02* (2006.01)
*A61K 47/06* (2006.01)

(52) U.S. Cl. .................... 424/489; 424/724; 514/770
(58) Field of Classification Search .................. None
See application file for complete search history.

(56) References Cited

U.S. PATENT DOCUMENTS

| | | | |
|---|---|---|---|
| 2,885,366 A | 5/1959 | Iler et al. |
| 3,785,798 A | 1/1974 | Horai et al. |
| 3,826,670 A | 7/1974 | Rees et al. |
| 4,069,311 A | 1/1978 | Mannara |
| 4,129,645 A | 12/1978 | Barnett et al. |
| 4,169,069 A | 9/1979 | Unger et al. |
| 4,349,456 A | 9/1982 | Snowman |
| 4,444,746 A | 4/1984 | Harvey et al. |
| 4,464,317 A | 8/1984 | Thies et al. |
| 4,533,484 A | 8/1985 | Walles et al. |
| 4,606,913 A | 8/1986 | Aronson et al. |
| 4,671,956 A | 6/1987 | Bouillon et al. |
| 4,769,080 A | 9/1988 | Clark et al. |
| 4,891,211 A | 1/1990 | Winston |
| 4,931,362 A | 6/1990 | Zsifkovits et al. |
| 4,988,744 A | 1/1991 | Yamamoto |
| 5,165,914 A | 11/1992 | Vlock |
| 5,200,334 A | 4/1993 | Dunn et al. |
| 5,269,840 A | 12/1993 | Morris et al. |
| 5,292,801 A | 3/1994 | Avnir et al. |
| 5,387,622 A | 2/1995 | Yamamoto |
| 5,455,048 A | 10/1995 | Lahmani et al. |
| 5,500,223 A | 3/1996 | Behan et al. |
| 5,520,917 A | 5/1996 | Mizuguchi et al. |
| 5,556,617 A | 9/1996 | Ribier et al. |
| 5,587,170 A | 12/1996 | Caisey et al. |
| 5,591,453 A | 1/1997 | Ducheyne et al. |
| 5,607,664 A | 3/1997 | Ascione et al. |
| 5,650,311 A | 7/1997 | Avnir et al. |
| 5,670,209 A | 9/1997 | Wyckoff |
| 5,672,301 A | 9/1997 | Orly et al. |
| 5,691,060 A | 11/1997 | Levy |
| 5,756,073 A | 5/1998 | Miller et al. |
| 5,785,977 A | 7/1998 | Breithbarth |
| 5,876,701 A | 3/1999 | Wong et al. |
| 5,879,716 A | 3/1999 | Katz et al. |
| 5,912,016 A | 6/1999 | Perrier et al. |
| 5,914,101 A | 6/1999 | Tapley et al. |
| 6,037,000 A | 3/2000 | Chang et al. |
| 6,074,629 A | 6/2000 | Kostinko et al. |
| 6,077,522 A | 6/2000 | Scher et al. |
| 6,090,399 A | 7/2000 | Ghosh et al. |

(Continued)

FOREIGN PATENT DOCUMENTS

AU 764016 B2 5/2000

(Continued)

OTHER PUBLICATIONS

Lal et al., "Silica Nanobubbles Containing an Organic Dye in a Multilayered Organic/Inorganic Heterostructure with Enhanced Luminescence," Chem. Mater. 2000, 12, pp. 2632-2639.*
Midmore, B.R., "Preparation of a Novel Silica-Stabilized Oil/Water Emulsion" Colloids and Surfaces A: Physicochemical and Engineering Aspects, vol. 132, pp. 257-265 (1998).
Mamoru Aizawa et al., "Preparation of Spherical Hydrous Silica Oxide Particles under Acidic Condition via Sol-Gel Processing," Journal of Sol-Gel Science and Technology 19, 329-332, 2000.
C. Barbe et al., "Sol-Gel Microspheres and nanospheres for controlled release applications," #293, pp. 545-546, 2002 Controlled Release Society 29th Annual Meeting Proceedings.
Federal Register, vol. 67, No. 94, and 40CFRo Part 180, 2002.

(Continued)

*Primary Examiner* — James H Alstrum Acevedo
(74) *Attorney, Agent, or Firm* — Lowe, Hauptman, Ham & Berner, LLP

(57) ABSTRACT

Substantially leachless, agent-encapsulating sol-gel particles, methods of preparing same and products containing same are provided.

15 Claims, 2 Drawing Sheets

U.S. PATENT DOCUMENTS

| | | | |
|---|---|---|---|
| 6,132,773 | A | 10/2000 | Amiche |
| 6,143,280 | A | 11/2000 | Pike et al. |
| 6,197,757 | B1 | 3/2001 | Perrier et al. |
| 6,238,650 | B1 | 5/2001 | Lapidot et al. |
| 6,242,099 | B1 | 6/2001 | Grandmontagne et al. |
| 6,251,313 | B1 | 6/2001 | Deubzer et al. |
| 6,280,746 | B1 | 8/2001 | Arquette et al. |
| 6,303,149 | B1 | 10/2001 | Magdassi et al. |
| 6,315,986 | B1 | 11/2001 | Wong et al. |
| 6,337,089 | B1 | 1/2002 | Yoshioka et al. |
| 6,436,375 | B1 | 8/2002 | Lapidot et al. |
| 6,468,509 | B2 | 10/2002 | Lapidot et al. |
| 6,495,352 | B1 | 12/2002 | Brinker et al. |
| 6,607,713 | B1 | 8/2003 | Chodorowski et al. |
| 6,616,947 | B1 | 9/2003 | Depuis |
| 6,855,335 | B2 | 2/2005 | Seok et al. |
| 7,585,521 | B2 * | 9/2009 | Barbe et al. .......... 424/501 |
| 2002/0064541 | A1 | 5/2002 | Lapidot et al. |
| 2005/0037087 | A1 | 2/2005 | Lapidot et al. |

FOREIGN PATENT DOCUMENTS

| | | |
|---|---|---|
| DE | 19811900 | 9/1999 |
| EP | 0281034 | 9/1988 |
| EP | 0 462 388 A2 | 12/1991 |
| EP | 0581651 | 2/1994 |
| EP | 0 680 753 A2 | 11/1995 |
| EP | 0934773 | 8/1999 |
| EP | 0 972 563 A1 | 1/2000 |
| FR | 2703927 | 10/1994 |
| FR | 2774906 | 8/1999 |
| FR | 2780901 | 1/2000 |
| GB | 1319991 | 6/1973 |
| GB | 2416524 | 2/2006 |
| JP | 01-113436 A | 5/1989 |
| JP | 22867 | 1/1990 |
| JP | 02-040302 A | 2/1990 |
| JP | 2251240 | 10/1990 |
| JP | 03-229634 A | 10/1991 |
| JP | 07-173452 A | 7/1995 |
| JP | 09-110463 A | 4/1997 |
| JP | 09-235217 A | 9/1997 |
| WO | 00/09652 | 2/0000 |
| WO | 94/04261 A1 | 3/1994 |
| WO | 97/18267 | 5/1997 |
| WO | 98/31333 | 7/1998 |
| WO | 99/03450 A1 | 1/1999 |
| WO | 00/25761 | 5/2000 |
| WO | 00/47236 A1 | 8/2000 |
| WO | 00/71084 | 11/2000 |
| WO | 00/72806 | 12/2000 |
| WO | 01/12221 A1 | 2/2001 |
| WO | 01/13924 A1 | 3/2001 |
| WO | 01/80823 | 11/2001 |
| WO | 02/085113 A1 | 10/2002 |
| WO | 03/034979 A2 | 5/2003 |
| WO | 03/039510 | 5/2003 |
| WO | 03/066209 | 8/2003 |
| WO | 2004/069216 | 8/2004 |
| WO | 2005/009604 | 2/2005 |
| WO | 2007/000316 A1 | 1/2007 |
| WO | 2007/015243 | 2/2007 |
| WO | 2007/015243 A2 | 2/2007 |
| WO | 2007/036939 A2 | 4/2007 |
| WO | 2008/002637 A2 | 1/2008 |

OTHER PUBLICATIONS

M. A. Butler et al., "An emulsion method for producing fine, low density, high surface area silica powder from alkoxides," Journal of Materials Science 31 (1996) 1675-1680.

H. Tatapudy et al., "Benzoyl Peroxide Microcapsules. I. Preparation of core material," Indian Drugs 32(6), 239-48, 1995.

D. Avnir et al., "Organic fluorescent dyes trapped in silica and silica-titania thin films by the sol-gel method. Photophysical, film and cage properties." Journal of Non-Crystalline Solids 74 (1985) 395-406.

Hou et al., "Improvement of photofatigue resistance of spirooxazine entrapped in organic-inorganic composite synthesized via the sol-gel method," SPIE vol. 2288 Sol-Gel Optics III, 328-339, 1994.

Bugnon, P, "Surface treatment of pigments. Treatment with inorganic materials", Progress in Organic Coatings, vol. 29, pp. 39-43, (1996).

Hall, S.B., et al., "Cocondensation of Organosilica Hybrid Shells on Nanoparticle Templates: A Direct Synthetic Route to Functionalized Core—Shell Colloids",Langmuir, vol. 16, pp. 1454-1456, (2000).

Haq, I., et al., "Preparation and properties of uniform coated inorganic colloidal particles 9. Titania on copper compouns", Colloids and Surfaces A: Physicochemical and Engineering Aspects, vol. 81, pp. 153-159, (1993).

Hench, L.L., et al., "The Sol-Gel Process",Chem. Rev. vol. 90, pp. 33-72, (1990).

Hsu, W.P., et al., "Paper Whiteners I. Titania Coated Silica", Journal of Colloid and Interface Science, vol. 156, pp. 56-65, (1993).

Iler, R., "Silica Gels", The Chemistry of Silica, pp. 510-533, (1979).

Kumar, M.N.V. Ravi, "Nano and Microparticles as Controlled Drug Delivery Devices", J. Pharm. Pharmaceutic. Sci. 3(2)234-258, (2000).

Lapidot, N., et al., "Advanced Sunscreens: UV Absorbers Encapsulated in Sol-Gel Glass Microcapsules", Journal of Sol-Gel Science and Technology, vol. 26, pp. 67-72, (2003).

Matijevic, E., et al, "Note Coating of Nanosize Silver Particles with Silica", Journal of Colloid and Interface Science, vol. 221, pp. 133-136, (2000).

Mikrajuddin, F., et al., "Stable photoluminescence of zinc oxide quantum dots in silica nanoparticles matrix prepared by the combined sol-gel and spray drying method", Journal of Applied Physics, vol. 89, pp. 6431-6434, (2001).

Nakatsuka, M., et al., "Surface Modification of Inorganic Pigments with Organic UV Absorbers",Colloid and Surfaces, vol. 34, pp. 323-334, (1988/89).

Osseo-Asare, K., "Hydrolysis of Silicon Alkoxides in Microemisions", Surfactan Sci. Sek., vol. 42, pp. 147-188, (2000).

Rottman, C., et al, "Advanced Sunscreens: UV Absorbers Entrapped in Glass Microcapsules", Euro Cosmetics, pp. 20-22, (2000).

Rottman, C., et al. "Sol-Gel Products News: Advanced Sunscreen: UV Absorbers Entrapped in Sol-Gel Glass Microcapsules", Journal of Sol-Gel Science and Technology, vol. 23, pp. 268-270, (2002).

M.P.B van Bruggen, "Preparation and Properties of colloidal Core-Shell Rods with Adjustable Aspect Ratios", Langmuir, vol. 14, pp. 2245-2255, (1998).

Sol-Gel Science, The Physics and Chemistry of Sol-Gel Processing, C. Jeffrey Brinker, George W. Scherer, May 1990, (pp. 562-563).

Iqball Gill et al. "Encapsulation of Biologicals within Silicate, Siloxane, and Hybrid Sol-Gel Polymers: An Efficient and Generic Approach", J. Am. Chem. Soc. vol. 120, pp. 8587-8598, (1998.

Duyan Dai, A study on the Technique of Preparing Microcapsules Via In Situ Polymerization and the Application Thereof, Journal of Tianjin Institute of Textile Science and Technology, 1994, 13 (1), 95-101. (English translation from Chinese).

* cited by examiner

AGENT-ENCAPSULATING MICRO- AND NANOPARTICLES, METHODS FOR PREPARATION OF SAME AND PRODUCTS CONTAINING SAME

FIELD AND BACKGROUND OF THE INVENTION

The present invention relates to substantially non-leachable sol-gel particles and, more particularly, to sol-gel micro- and nanoparticles encapsulating one or more agents (e.g., colorants), characterized by unprecedented stability to leaching or migration of the agents from therein. The present invention further relates to a method of producing the particles of the invention and to products containing the particles of the invention, such as, for example, cosmetic, and oral care colored products.

Coloring agents, which are also referred to herein as colorants, such as dyes, pigments, colors and lakes are well known in the art and are widely used in a variety of fields. However, as many of the presently known colorants are toxic, chemically reactive and/or water soluble, their use is severely limited.

"FD&C" and "D&C" colors are colorants that are allowed for use in food, drugs and cosmetics by governmental regulatory authorities, such as the FDA. These colors are typically water-soluble and as such, their applications are often limited by their tendency to leach into parts of the formulation where their presence is undesired (for example, in striped toothpaste) or to form complexes with other ingredients, such as, for example, proteins, which are present in the formulations.

"FD&C" colors can be formulated as lakes, where they are adsorbed on inorganic substrates such as alumina, titania or zirconia. U.S. Pat. No. 4,444,746 teaches, for example, the use of such lakes in dentifrices. The lake is dispersed throughout a dentifrice medium and is aimed at preventing dissolution of the water-soluble dye. Nevertheless, while lakes may be useful in preventing the dissolution of water-soluble colors, they do not prevent the colors migration to the surrounding medium.

Colors and dyes which do not belong to the "FD&C" colors can optionally be used in some cosmetic applications. However, due to the relative toxicity of such coloring agents, their use is limited by the proviso that they would not contact the skin.

Other water-based colors, dyes or lakes, which are excluded for use in food, drugs and cosmetics, are used in various industrial applications. The use of such industrial colors is often limited by their high chemical reactivity, which results in high susceptibility thereof to chemical/photochemical attack.

One of the prevalent ways to overcome the limitations associated with using coloring agents in various applications is external encapsulation of the colorants. External encapsulation of colors, dyes and lakes may prevent undesired leaching and/or contact and may further protect the colorants from other environmental components, thereby increasing their applicable value.

However, apart from providing protection and preventing leaching and/or contact of the colorants, efficient and applicable colorants encapsulation further depends on other parameters such as particles size, particles shape, transparency, toxicity of the encapsulating matrix and more, particularly in cases where the encapsulated colorants are used in oral care, pharmaceutical and/or cosmetic products.

More specifically, a preferred size of colorant-containing particles is in the several microns range. Using colored particles that have lager size, e.g., over 10 microns, is undesired since mixing such particles with formulations for oral care (e.g., toothpaste) and cosmetics would result in dots-like colored medium, rather than continuously colored product. Moreover, the tinting power of large pigments is severely affected by large particles size. In addition, large particles usually impair a gritty feeling, which is highly undesirable in, for example, cosmetic products.

Particles encapsulating colorants should further preferably have a spherical shape, which provides for a better feeling of the final product and for a continuous coloring effect.

The encapsulating medium should also be transparent, so as to maintain the coloring effect of the encapsulated colorant.

Encapsulation of different ingredients can be obtained using both organic and inorganic matrices. Typical organic matrices include organic and bioorganic polymers. Such polymers are inherently more susceptible to chemical and photochemical damage as compared with inorganic polymers and are highly sensitive to shear forces, osmotic pressure, heat, etc. Therefore, organic matrices typically tend to release the ingredients contained therein into the surrounding medium, hence failing to supply sufficient stability and localization of the colored product. Furthermore, many of the presently known organic matrices used for encapsulation of water-soluble ingredient are often characterized by relative toxicity, which prevents their use in, for example, food, drug, oral care and cosmetic formulations. Thus, encapsulation of colorants in inorganic matrices, which are typically more stable and often less toxic, is preferable.

External encapsulation of coloring agents has been practiced to some extent, using both organic and inorganic encapsulation matrices and typically involves the production of water-insoluble pigments containing water-soluble colorants.

U.S. Pat. No. 4,769,080, for examples, teaches the use of a layered anion exchange material, preferably an aluminate, which is contacted with a liquid medium containing the dissolved dye, to thereby adhere the dye within the layered material.

GB Patent No. 1,319,991 teaches preparation of colored resins containing non-toxic water-soluble dyes as a water impervious cross-linked synthetic resin for use in toothpastes. Water-soluble monomers such as urea formaldehyde, melamine formaldehyde, melamine-urea formaldehyde and phenol formaldehyde are used according to the teachings of this reference to form the water-insoluble resins. However, it should be noted that, as is well known in the art, formaldehyde is a toxic agent and hence its use in, for example, oral care and cosmetic products is highly undesirable as traces thereof can be released over time.

U.S. Pat. No. 5,756,073 discloses a striped dentifrice (e.g., a paste or gel) in which the colorant is loaded within a substantially non-fracturable matrix of a partially cross-linked melamine-urea-formaldehyde polymer. The polymer is in the form of particles having a size range of from about 2 to 70 microns. The dentifrice, according to the teachings of this reference, may also contain a scavenger compound, which is aimed at inactivating or binding up any un-reacted cross-linking agent (i.e., formaldehyde). The inclusion of such a scavenger in the formulation demonstrates the severe limitations associated with the incorporation of formaldehyde-containing polymers in, for example, oral care products.

U.S. Pat. No. 4,069,311 discloses the formation of small colored globules or particles, obtained by dispersing a speckling material and a binder such as a thermoplastic resin, gum, gel, paraffin, wax, polymer and high fatty acid and salts thereof, in water. The speckling material used in this patent is evidently water-insoluble and hence this method cannot be used with water-soluble coloring agents such as the FD&C colors.

U.S. Pat. No. 4,533,484 also teaches a method of preparing water-insoluble pigment particles, which is effected by contacting water-soluble dyes with a polymer that comprises an alkyl-2-oxazolidinone moiety.

WO 97/18267 and U.S. Pat. No. 6,037,000 teach a process of encapsulating colored lakes within a substrate such as a high-density polyethylene material, by means of melt and spray-congealing, in which particles that are substantially impervious to water or other solutes of choice are formed. A secondary coating comprised of another substance, such as petrolatum, may optionally be added to the matrix so as to virtually eliminate dye migration. According to the teachings of these references, the size of the obtained pigment particles ranges between 5 and 35 microns. As is discussed hereinabove, such relatively large particles are undesirable in most of the colored formulations. As it is well known in the art that particles formed by spray-congealing processes have a size of at least few microns, it is impossible to produce by the process described in these references smaller particles.

Similarly, U.S. Pat. Nos. 5,876,701 and 6,315,986 disclose a lake-containing striped dentifrice in which the lake is stabilized by entraining in wax or in high-density polyethylene matrices in a melt process. As this process involves the same general technique used in WO 97/18267 and U.S. Pat. No. 6,037,000, the obtained particles are evidently of large size and hence the use thereof is limited.

All the formulations described hereinabove employ organic or bioorganic matrices for encapsulating the colorants. As is further discussed hereinabove, the use of such matrices is often limited due to their relatively poor stability and toxicity. Furthermore, some of the processes described hereinabove are further limited by the relatively large size of the particles produced thereby.

As is further discussed hereinabove, inorganic polymers often present a better choice as encapsulation matrices for colorants, particularly in cases where the colored products are directed to food, drug, oral care or cosmetic applications. Silica, which is also known by its chemical name silicon dioxide, is one of the presently preferred inorganic substances that can be used as an encapsulation matrix for such applications, as it is a safe and stable chemical, which is allowed for use in food products (see, for example, Federal Register, Volume 67, Number 94 and 40CFRo Part 180, 2002).

U.S. Pat. No. 6,074,629 discloses a dentifrice containing dye-absorbing amorphous silica granules. The granules are characterized by linseed-oil absorption of at least about 150 cc/100 grams and by an average particle size of about 400 micron to about 600 micron and can be either spherical or non-spherical. The amorphous silica granules serve as an absorbent of an FD&C dye or other coloring agent, so as to form a darker portion of the dentifrice, such that a speckled appearance of the dentifrice is obtained. As is discussed hereinabove, the large particles produced by such a process result in a final product that is characterized by both grittiness and possible abrasiveness. Furthermore, as the process involves absorbance of the colorant by the silica granules from a mixture containing all the components comprising the dentifrice, the silica granules cannot serve as an efficient matrix for preventing leakage and migration of the dye.

U.S. Pat. No. 6,143,280 also teaches a method of adhering dye to silica particles. Porous silica slurry is used as a substrate for deposition of colorant-containing aluminum hydroxide within the pores. The product is then milled to obtain non-spherical particles having a size of 5 to 15 micron. Again, such a process results in large and non-spherical particles, which affect both the feeling and the coloring effect of the final product.

EP 0 581 651 teaches a method of producing spherical fine particles having a coloring pigment enclosed therein. The method involves coating of the pigments with a metal oxide either by an interface reaction process or by preparing a gel from an aqueous solution of metal oxide sol. The pigments used in this method are water-insoluble organic or inorganic pigments. The metal oxide coating provides for spherical shape of the particles, which contributes to even dispersion of the particles in make up formulations, and affords the desired vivid color. The size of the final particles is 0.1 to 50 micron in diameter, as required for obtaining the desired feeling and coloring effects. Nevertheless, EP 0 581 651 fails to teach a method of encapsulating water-soluble colorants, and hence the method described therein cannot be utilized with colorants such as FD&C colors, which, as stated above, are water-soluble colorants.

Japanese Patent Application No. 7-238983 discloses a cosmetic material that contains a colored metal oxide gel. The gel is produced by adding a metal alkoxide to a water-in-oil type emulsion containing a water-soluble colorant. The metal oxide gel is obtained in the form of spherical particles, having a size of 0.1 to 500 micron. The approach utilized in this reference, namely, formation of colored particles via a sol-gel process, is aimed at producing colored particles which are spherical, having a relatively small size and are capable of preventing leaching and/or migration of the colorant. However, as is discussed in detail hereinbelow, although such a method of encapsulating colorants appears to produce particles that are characterized by all the parameters required for efficient encapsulation, while considering the limitations that typically accompany encapsulation of various ingredients by such a sol-gel process, it is unlikely to expect that such particles would completely prevent leaching and/or migration of the encapsulated colorant. In this respect it should be noted that although this reference teaches the stability of the colored spheres upon heating in air, it fails to teach whether the obtained spheres can prevent leaching of the dye therefrom in various formulations.

Preparation of spherical hydrous silica oxide particles under acidic conditions is also described by Aizawa et al. [M. Aizawa, S. Kitajima, M. Ohsawa and W. Yang, *J. Sol-Gel Sci. Tech.* 19, 329-332, 2000]. Particles of 10 to 100 microns entrapping Rhodamine 6G, a hydrophilic dye, are prepared in emulsions, using tetraethyl orthosilicate (TEOS), ethyl acetate and acetic acid/water system, and hydrochloric acid as a catalyst. The particles obtained by this process are dense and clear and its final shape, i.e., spherical particles, non-spherical powder or homogeneous solutions, is determined by the TEOS/ethyl acetate/acetic acid ratio used. The process disclosed in this reference is also based on a simple sol-gel process which, as is discussed hereinabove, typically fails to provide non-leachable particles.

Barbe et al. [C. Barbe, R. Beyer, L. Kong, M. Blackford, R. Trautman and J. Bartlett, *Controlled Release Society 29th annual meeting proceedings,* No. 293] also teach the preparation of silica microspheres and nanospheres entrapping a colorant. According to the teachings of Barbe et al., water-in-oil emulsions of the dye Orange II, tetramethyl orthosilicate (TMOS), methanol, water and surfactants are used to form silica spheres entrapping the dye, using either acidic or basic catalysis. The size of the obtained spheres is between 50 nm to 50 microns. However this reference further teaches, upon investigating the release kinetics of the dye from the spheres, that such a system can serve for controlled release applications since the obtained particles were found to release the entrapped dye. The research conducted by Barbe et al. demonstrates the inefficiency of silica particles obtained by a simple sol-gel process to completely prevent leaching and/or migration of the dye therefrom.

Hence, although the prior art teaches various methods for encapsulating water-soluble colorants, none of these methods provides a product which is non-toxic, evenly colored and is further characterized by small particles size, spherical particles shape and ability to prevent leaching and/or migration of the entrapped colorant.

As these parameters are all required for efficient use of the encapsulated colorant in various applications, such as, for example, oral care, food, drug and cosmetics applications, there is a widely recognized need for, and it would be highly advantageous to have, a method of encapsulating colorants devoid of the above limitations. The development of such a method can be further utilized for producing leachless particles that encapsulate other agents while preventing their leaching.

SUMMARY OF THE INVENTION

According to one aspect of the present invention there is provided a method of preparing substantially leachless, agent-encapsulating sol-gel particles. The method comprises emulsifying an inner phase containing at least one agent and at least one first sol-gel precursor in an outer phase containing a dispersing medium, for obtaining initial sol-gel particles encapsulating the at least one agent, and reacting the initial sol-gel particles with at least one second sol-gel precursor, thereby obtaining the substantially leachless, agent-encapsulating sol-gel particles.

According to further features in preferred embodiments of the invention described below, the method further comprises, prior to reacting the initial sol-gel particles, washing the initial sol-gel particles with at least one solvent, preferably an organic solvent.

According to still further features in the described preferred embodiments the method further comprises, prior to reacting the initial sol-gel particles, and following the washing, drying the initial sol-gel particles.

According to still further features in the described preferred embodiments the method further comprises, following the reacting of the initial sol-gel particles, washing the substantially leachless sol-gel particles with at least one solvent, preferably an organic solvent.

According to still further features in the described preferred embodiments the method further comprises, following the washing, drying the substantially leachless sol-gel particles.

According to further features in preferred embodiments of the invention described below, an average particles size of the substantially leachless sol-gel particles ranges between 0.05 micron and 5 microns in diameter.

According to still further features in the described preferred embodiments the substantially leachless sol-gel particles are spherical particles.

According to still further features in the described preferred embodiments the substantially leachless sol-gel particles are transparent.

According to still further features in the described preferred embodiments a surface area of the substantially leachless sol-gel particles ranges between $0.01 \text{ m}^2/\text{gram}$ and $5 \text{ m}^2/\text{gram}$.

According to still further features in the described preferred embodiments the concentration of the at least one agent ranges between 0.1 weight percentages and 20 weight percentages of the substantially leachless sol-gel particles.

Hence, according to another aspect of the present invention there are provided substantially leachless, transparent, agent-encapsulating sol-gel particles having a spherical shape, an average particles size that ranges between 0.05 micron and 5 microns in diameter and a surface area that ranges between $0.01 \text{ m}^2/\text{gram}$ and $5 \text{ m}^2/\text{gram}$, being prepared by the method described hereinabove.

According to further features in preferred embodiments of the invention described below, the substantially leachless sol-gel particles are characterized by leaching of no more than 2 weight percentages of the at least one agent from therein upon mixing and agitating the sol-gel particles with an extraction medium for at least 7 days at 40° C.

Hence, according to yet another aspect of the present invention there are provided substantially leachless, transparent, agent-encapsulating sol-gel particles, characterized by leaching of no more than 2 weight percentages of the agent upon mixing and agitating the sol-gel particles with an extraction medium for at least 7 days at 40° C.

According to further features in preferred embodiments of the invention described below, the agent is water-soluble.

According to still further features in the described preferred embodiments the agent is a colorant, preferably a water-soluble colorant.

According to still further features in the described preferred embodiments the water-soluble colorant is selected from the group consisting of an FD&C color and a natural colorant.

According to still further features in the described preferred embodiments the FD&C color is selected from the group consisting of EXT.D&C Green No. 1, EXT.D&C Yellow No. 7, EXT.D&C Yellow No. 1, EXT. D&C Orange No. 3, FD&C Red No. 4, D&C Orange No. 4, FD&C Yellow No. 6, D&C Red No. 2, D&C Red No. 33, EXT.D&C Yellow No. 3, FD&C Yellow No. 5, D&C Brown No. 1, D&C Black No. 1, FD&C Green No. 3, FD&C Blue No. 1, D&C Blue No. 4, D&C Red No. 19, D&C Red No. 37, EXT. D&C Red No. 3, D&C Yellow No. 8, D&C Orange No. 5, D&C Red No. 21, D&C Red No. 22, D&C Red No. 28, D&C Red No. 27, D&C Orange No. 10, D&C Orange No. 1, FD&C Red No. 3, D&C Yellow No. 1, D&C Yellow No. 10, D&C Green No. 8, EXT. D&C Violet No. 2, D&C Green No. 5 and FD&C Blue No. 2.

According to still further features in the described preferred embodiments the natural coloring material is selected from the group consisting of kuchinashi blue, kuchinashi yellow, shisonin, grapeskin extract, cacao pigment, safflower yellow, hibiscus pigment, lac dye, cochineal, shikon, beet red, brazilin curcumin, riboflavin, lutein, carotenoids, annatto), paprika, carminic acid, carmin, anthocyanins, cabbage, chlorophyll, chlorophyllin, copper-chlorophyll, copper-chlorophyllin, caramel and carbomedicinalis.

According to still further features in the described preferred embodiments the water-soluble colorant is a luminescent dye, such as, for example, a fluorescent dye, a phosphorescent dye, a chemiluminescent composition and a near IR (NIR) dye.

According to still further features in the described preferred embodiments the extraction medium is an aqueous medium.

According to still further features in the described preferred embodiments the inner phase further comprises a water miscible solvent.

According to still further features in the described preferred embodiments the water miscible solvent further comprises an acid.

According to still further features in the described preferred embodiments the inner phase further comprises at least one surfactant. Preferably, the surfactant is selected from the group consisting of an anionic surfactant, a cationic surfactant, an amphoteric surfactant, a nonionic surfactant and mixtures thereof. Further preferably, the surfactant is selected from the group consisting of Polysorbate 20, Polysorbate 40, Polysorbate 60, Polysorbate 65, Polysorbate 80, Polysorbate 85, Sorbitan laurate, Sorbitan palmitate, Sorbitan stearate, Sorbitan tristearate, Sorbitan oleate, Sorbitan sesquioleate, trioleate Sorbitan, Simulsol 988/989 (PEG-7 Hydrogenated Castor oil), PEG-35-Castor oil, PEG-40-Castor oil, PEG-25-Hydrogenated Castor oil, PEG-40-Hydrogenated Castor oil, PEG-60-Hydrogenated Castor oil, Mix sorbitan ester, Lecithin, sodium oleate and poloxamers.

According to still further features in the described preferred embodiments the outer phase further comprises at least one oil miscible solvent. Preferably, the oil miscible solvent is selected from the group consisting of castor oil, oleic acid, decanol, octanol, heptanol, nonanol, linoleic acid, ethyl linoleate, alpha linolenic acid, gamma linolenic acid, stearidonic acid, neuronic acid, palm oil, corn oil, coconut oil, kernel oil, sesame oil, cottonseed oil, safflower oil, flaxseed oil, amber oil, soybean oil, olive oil, almond oil, peanut oil, aniseed oil, bay oil, bergamot oil, cajeput oil, camphor oil, capsicum oleoresin, caraway oil, cardamom oil, cassia oil, cedarwood oil, cinnamon oil, citronnela oil, clove bud oil, clove oil, copaiba balsam oil, coriander oil, cumin seed oil, dill oil, eucalyptus oil, fennel oil, geranium oil, ginger oleoresine, juniperberry oil, lavender oil, lemon oil, methyl salicylate, neroli oil, peppermint oil, pine oil, rosemary oil, spearmint oil, thyme oil red/white, tolu balsam, turpentine oil, Cremophor EL (polyethoxylated castor oil surfactant), mono, di and tree glycerides of sorbitan tristearate, lauric acid, citric acid, lactic acid, glyceryl, linoleate, soy oil, edible fats, capric, caprlic, oleyl alcohol erucic ester, vegetable fats, ethyl oleate, n-hexadecane, 1-hexadecane, cetylic alcohol, palmitic acid, cetylpalmitate, isopripylmyristate, oleum ricini, oleum arachidis, cera perliquida, paraffinum perliquidum, lauromagrogols, nonoxynols, octoxynoles and poloxamers.

According to still further features in the described preferred embodiments the outer phase further comprises at least one surfactant, as is detailed hereinabove.

According to still further features in the described preferred embodiments the outer phase further comprises at least one viscosity modifying agent.

According to still further features in the described preferred embodiments the dispersing medium is a hydrophobic dispersing medium.

According to still further features in the described preferred embodiments, reacting the initial sol-gel particles is performed in the presence of a catalyst, preferably an acidic catalyst.

According to still further features in the described preferred embodiments the first and the second sol-gel precursor are each independently selected from the group consisting of a metal alkoxide monomer, a semi-metal alkoxide monomer, a metal ester monomer, a semi-metal ester monomer, a silazane monomer, a monomer having the formula $M(R)_n(P)_m$, whereas M is a metal or a semi metal, R is a hydrolyzable substituent, n is an integer from 2 to 6, P is a non-polymerizable substituent and m is and integer from 0 to 6, a partially hydrolyzed polymer thereof, a partially condensed polymer thereof and a combination thereof.

According to still further features in the described preferred embodiments the metal is selected from the group consisting of Si, Ti, Zr, Ni, Al and Zn.

According to still further features in the described preferred embodiments the first sol-gel precursor is a water-soluble monomer having the formula $M(R)_n(L)_m$, whereas M is a metal or a semi metal, R is a hydrolyzable substituent, n is an integer from 2 to 6, L is a hydrolyzable water-soluble substituent and m is and integer from 1 to 6.

According to still further features in the described preferred embodiments each of the water-soluble substituents L is independently selected from the group consisting of glycol, glycol ester, glycerol, sugar and derivatives thereof.

According to still another aspect of the present invention there is provided a colored cosmetic product stable to color leaching and/or migration, which comprises the substantially leachless, colorant-encapsulating sol-gel particles of the present invention and a cosmetically acceptable carrier, whereby after storage, substantially no significant amount of the colorant is observable as migrating into the carrier.

According to further features in preferred embodiments of the invention described below, the colored cosmetic product is in the form of an emulsion, a cream, an aqueous solution, an oil, an ointment, a paste, a gel, a lotion, a milk, a suspension, a powder, a foam, a shampoo, a hair conditioner, a lacquer, a makeup and a solid stick.

According to still further features in the described preferred embodiments the colored cosmetic product is selected from the group consisting of a lipstick, an eye shadow, a blush, a lacquer, a glitter, a shower gel, an oral care product (e.g., a dentifrice), a lip-gloss, a cream, a soap, a mascara, a shampoo and an anti-aging product.

According to an additional aspect of the present invention there is provided a method of preparing the colored cosmetic product of the present invention. The method comprises preparing the substantially leachless, colorant-encapsulating sol-gel particles, according to the method described hereinabove and mixing the substantially leachless colorant-encapsulating sol-gel particles with a cosmetic acceptable carrier.

According to yet an additional aspect of the present invention there is provided a multicolored dentifrice composition stable to color bleeding. The composition comprises a plurality of components, wherein at least one component containing the substantially leachless, colorant-encapsulating sol-gel particles of the present invention, whereby after storage, substantially no significant amount of the colorant is observable as migrating into any other dentifrice component. The composition can be a striped composition or a speckled composition.

According to still an additional aspect of the present invention there is provided a method of preparing the multicolored dentifrice composition of the present invention. The method comprises preparing a plurality of different colored dentifrice components being in physical interfacial contact therebetween, wherein at least one of the components containing the substantially leachless, colorant-encapsulating sol-gel particles of the present invention, prepared as described hereinabove.

According to a further aspect of the present invention there is provided a colored food additive stable to color leaching and/or migration, which comprises the substantially leachless, colorant-encapsulating sol-gel particles of the present invention and an edible carrier, whereby after storage, substantially no significant amount of the colorant is observable as migrating into the carrier.

According to yet a further aspect of the present invention there is provided a colored article-of-manufacture stable to color leaching and/or migration, which comprises the substantially leachless, colorant-encapsulating sol-gel particles of the present invention and a suitable carrier, whereby after storage, substantially no significant amount of the colorant is observable as migrating into the carrier.

The colored article-of-manufacture can be, for example, a cosmetic product, a pharmaceutical product, a diagnostic agent, an oral care product, a food additive, a detergent, an ink composition, an antiperspirant, a coating, a packaging material, a paint, a cloth, a plastic, a toy and the like.

The present invention successfully addresses the shortcomings of the presently known configurations by providing substantially leachless, agent-encapsulating sol-gel particles and products containing same.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1A:
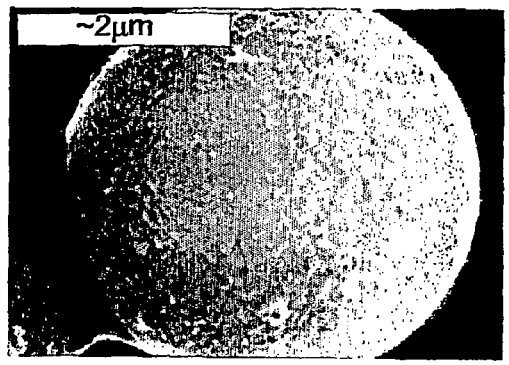
FIGS. 1a-b present SEM images of uncoated (FIG. 1a) and coated (FIG. 1b) colored silica microspheres prepared according to a preferred embodiment of the present invention.

The present invention is of substantially leachless sol-gel micro- and nanoparticles, which can be used as efficient agent-encapsulating particles in various applications. The substantially leachless sol-gel particles of the present invention are specifically useful as colorant-encapsulating particles in various colored products such as, for example, dentifrices and colored cosmetics, pharmaceutical and food products, ink compositions, diagnostic agents, packaging materials, paints, coatings, plastics, cloths and detergents, where preventing of leaching and/or migration of the colorant is highly desirable.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Developing a method of external encapsulation of agents, which results in particles that efficiently entrap the agent while diminishing its leaching from therein, is highly desirable. Such a method is evidently particularly advantageous in cases where the encapsulated agent should not be in contact with the environment due, for example, to high toxicity or high reactivity of the agent. Such cases include, for example, applications that involve radioactive agents, chemically reactive agents or cosmetic active ingredients that are not allowed to contact the skin. Efficient external encapsulation of agents is further highly advantageous in the production of colored compositions for use in, e.g., food, cosmetic and oral care products. As is described hereinabove, most of the presently known colorants are either water-soluble and hence tend to leach or migrate into parts of the formulation where their presence is undesired, or are chemically reactive and hence unstable and/or toxic.

A superior media for encapsulating agents is doping within sol-gel matrices. In this method, monoliths, particles or other forms (such as thin layers, or fibers) are prepared, and the agent is encapsulated in the pores of the sol-gel matrix. Encapsulation in sol-gel matrices is one of the most advantageous presently known encapsulation methods as it enables to perform the process under mild conditions that do not affect the encapsulated agent and to control important parameters of the obtained product such as, for example, hydrophobic/hydrophilic character, ionic character, size and shape.

As is described hereinabove, external encapsulation of colorants using sol-gel matrices has been practiced to some extent. For example, Japanese Patent Application No. 7-238983 discloses a cosmetic material in which a colored metal oxide gel is prepared by a sol-gel process. The gel is produced by adding a metal alkoxide to a water-in-oil type emulsion that contains a water-soluble colorant. The metal oxide gel is obtained in the form of spherical particles, having a size of 0.1 to 500 micron. The approach utilized in this reference, namely, formation of colored particles via a sol-gel process, is aimed at producing colored particles which are spherical, having a relatively small size and are capable of preventing leaching and/or migration of the colorant. However, although such a method of encapsulating colorants appears to produce particles that are characterized by all the parameters required for efficient encapsulation, as is discussed in detail hereinabove, it should be noted that while considering the limitations that typically accompany encapsulation of various ingredients by such a sol-gel process, it is unlikely to expect that such particles would completely prevent leaching and/or migration of the encapsulated colorant, as it is known in the art that sol-gel spheres obtained by the process utilized in Japanese Patent Application No. 7-238983 are characterized as a matrix that is capable of releasing the encapsulated agent from therein.

An example of the release capability of such sol-gel spheres is demonstrated, for example, by Barbe et al. [C. Barbe, R. Beyer, L. Kong, M. Blackford, R. Trautman and J. Bartlett, *Controlled Release Society* 29$^{th}$ *annual meeting proceedings,* No. 293], who teach a preparation of silica particles that entrap a colorant, which also involves water-in-oil emulsions and acidic or basic catalysis. Barbe et al. have investigated the release kinetics of the dye from the obtained spheres, and have found that such a system can serve for controlled release applications since the obtained particles were found to release the entrapped dye.

Hence, although the prior art teaches sol-gel particles encapsulating water-soluble colorants, as well as other agents, it fails to teach such particles that are substantially leachless and hence can serve as an efficient encapsulation medium in a variety of applications, as is discussed hereinabove and is further detailed hereinbelow.

While conceiving the present invention, it has been envisioned that preparing "double-layered" sol-gel microparticles, namely, sol-gel microspheres which are further reacted with sol-gel precursor(s) so as to form a second sol-gel layer coating the initial microspheres, would result in non-porous particles that could serve as a leachless encapsulating matrix.

While reducing the present invention to practice, it has indeed been found that using such a process resulted in substantially leachless sol-gel particles. As is detailed hereinbelow and in the Examples section that follows, the capability of these sol-gel particles to prevent leaching of an encapsulated agent has been demonstrated by a prolonged extraction assay.

Hence, according to one aspect of the present invention there is provided a method of preparing substantially leachless, agent-encapsulating sol-gel particles. The method is effected by emulsifying an inner phase, which contains one or more agent(s) to be encapsulated and one or more first sol-gel precursor(s), in an outer phase that contains a dispersing medium, so as to obtain initial sol-gel particles in which the agent is encapsulated, and thereafter reacting these initial sol-gel particles with one or more second sol-gel precursor(s).

The method, according to this aspect of the present invention, therefore includes two stages. In the first stage, initial sol-gel particles that encapsulate one or more agent(s) are prepared by emulsifying two different phases in the presence of sol-gel precursor(s), as is detailed hereinbelow. As is well known in the art, sol-gel particles obtained in such a process are porous particles and typically have free hydrolyzable groups at both the surface and pores thereof. Hence, in the second stage of the method, these hydrolyzable groups are reacted with a second sol-gel precursor, in a typical sol-gel process, which involves hydrolysis and condensation of the hydrolyzable groups, such that a second sol-gel layer is formed on the surface and within the pores of the particles. The second sol-gel layer thus provides for sealed surface and pores within the particles, and thereby efficiently prevents leaching of the encapsulated agent.

According to the present invention, the encapsulated agent can be any compound or composition that preventing its leaching from the encapsulating medium is desirable.

As is discussed hereinabove, representative examples of such agents include, without limitation, highly toxic agents, radioactive agents and chemically reactive agents. Specific examples of such agents include, without limitations, fragrances, pesticides, herbicides, detergents, diagnostic agents and the like.

As is further discussed in detail hereinabove, producing leachless encapsulating particles is particularly advantageous in cases where the encapsulated agent is water-soluble and therefore tends to leach when present in aqueous formulations. It should be noted in this respect that most of the formulations for human applications are typically aqueous formulations and hence producing leachless particles encapsulating water-soluble agents is highly desirable.

Hence, the method of the present invention is particularly useful when the encapsulated agent is a water-soluble agent.

Preferred agents that can benefit from leachless encapsulation are colorants. As is discussed in detail hereinabove, colorants that are presently widely used in various applications typically include FD&C colors, which are water-soluble, natural colors, or other colors which are not allowed for food, drug or cosmetic use due to high toxicity and/or chemical reactivity thereof.

A representative group of non-FD&C colorants that are widely used in a myriad of applications includes luminescent dyes such as fluorescent dyes, phosphorescent dyes, chemiluminescent compositions and near IR dyes.

Near IR dyes, for example, are typically used in, for example, welding of biological tissues, welding of polymers, laser protective eyewear, infrared filters, laser imaging, heat shielding glazing, security inks and military camouflage. Hence, leachless encapsulation of these near IR dyes is highly desirable.

Fluorescent dyes are typically used in, for example, cosmetic products, provided that they do not contact the skin, ink compositions, packaging materials, detergents and paints. Leachless encapsulation of fluorescent dyes is evidently highly desirable as well.

The use of FD&C colors in colored food, drug and cosmetic products is severely limited by their solubility in water, since these products typically include aqueous formulations and hence the colorant often migrates into parts of the formulation in which its presence is undesirable.

The use of colorants that do not belong to the FD&C family is also severely limited. Such colorants can be used, for example, in various cosmetic applications provided that they do not contact the skin, and hence should be efficiently encapsulated. Such colorants can further be used in other, non-human applications such as, for example, detergents, car paints, wall paints and more. Colorants which are used in these applications are typically characterized as toxic and/or chemically reactive and hence their contact with the environment should be avoided.

As preventing leaching and/or migration of colorants, water-soluble colorants in particular, is highly desirable, the method of the present invention is preferably directed toward the production of leachless particles encapsulating water-soluble colorants.

Representative examples of water-soluble colorants that are usable in this and other aspects of the present invention include, without limitation, FD&C colors such as EXT.D&C Green No. 1, EXT.D&C Yellow No. 7, EXT.D&C Yellow No. 1, EXT. D&C Orange No. 3, FD&C Red No. 4, D&C Orange No. 4, FD&C Yellow No. 6, D&C Red No. 2, D&C Red No. 33, EXT.D&C Yellow No. 3, FD&C Yellow No. 5, D&C Brown No. 1, D&C Black No. 1, FD&C Green No. 3, FD&C Blue No. 1, D&C Blue No. 4, D&C Red No. 19, D&C Red No. 37, EXT. D&C Red No. 3, D&C Yellow No. 8, D&C Orange No. 5, D&C Red No. 21, D&C Red No. 22, D&C Red No. 28, D&C Red No. 27, D&C Orange No. 10, D&C Orange No. 11, FD&C Red No. 3, D&C Yellow No. 11, D&C Yellow No. 10, D&C Green No. 8, EXT. D&C Violet No. 2, D&C Green No. 5 and FD&C Blue No. 2.

A comprehensive list of water-soluble colorants which are usable in the context of the present invention, according to their Color Index No. and name, their Japanese name and their FDA name is set forth in Table 1 below.

TABLE 1

| CI Number | Japanese name | FDA name | Color Index name |
|---|---|---|---|
| C.I. 10020 | Green No. 401 | (EXT. D & C Green No. 1) | Acid Green 1 |
| C.I. 10316 | Yellow No. 403-1 | (EXT. D & C Yellow No. 7) | Acid Yellow 1 |
| C.I. 13065 | Yellow No. 406 | (EXT. D & C Yellow No. 1) | Acid Yellow 36 |
| C.I. 14600 | Orange No. 402 | (EXT. D & C Orange No. 3) | Acid Orange 20 |
| C.I. 14700 | Red No. 504 | FD & C Red No. 4 | Food Red 1 |
| C.I. 15510 | Orange No. 205 | D & C Orange No. 4 | Acid Orange 7 |
| C.I. 15620 | Red No. 506 | | Acid Red 88 |
| C.I. 15985 | Yellow No. 5 | FD & C Yellow No. 6 | Food Yellow 3 |
| C.I. 16150 | Red No. 503 | | Acid Red 26 |
| C.I. 16155 | Red No. 502 | | Food Red 6 |
| C.I. 16185 | Red No. 2 | (D & C Red No. 2) | Acid Red 27 |
| C.I. 16255 | Red No. 102 | | Acid Red 18 |
| C.I. 17200 | Red No. 227 | D & C Red No. 33 | Acid Red 33 |
| C.I. 18820 | Yellow No. 407 | (EXT. D & C Yellow No. 3) | Acid Yellow 11 |
| C.I. 18950 | Yellow No. 402 | | Acid Yellow 40 |
| C.I. 19140 | Yellow No. 4 | FD & C Yellow No. 5 | Acid Yellow 23 |
| C.I. 20170 | Brown No. 201 | (D & C Brown No. 1) | Acid Orange 24 |
| C.I. 20470 | Black No. 401 | (D & C Black No. 1) | Acid Black 1 |
| C.I. 42052 | Blue No. 202 | | Acid Blue 5 |
| C.I. 42052 | Blue No. 203 | | Acid Blue 5 |
| C.I. 42053 | Green No. 3 | FD & C Green No. 3 | Food Green |
| C.I. 42085 | Green No. 402 | | Acid Green 3 |
| C.I. 42090 | Blue No. 1 | FD & C Blue No. 1 | Food Blue 2 |
| C.I. 42090 | Blue No. 205 | D & C Blue No. 4 | Acid Blue 9 |
| C.I. 42095 | Green No. 205 | | Acid Green 5 |
| C.I. 45100 | Red No. 106 | | Acid Red 52 |
| C.I. 45170 | Red No. 213 | (D & C Red No. 19) | Basic Violet 10 |
| C.I. 45170 | Red No. 214 | | Solv. Red 49 |
| C.I. 45170 | Red No. 215 | (D & C Red No. 37) | Solv. Red 49 |
| C.I. 45190 | Red No. 401 | (EXT. D & C Red No. 3) | Acid Violet 9 |
| C.I. 45350 | Yellow No. 202-1 | D & C Yellow No. 8 | Acid Yellow 73 |
| C.I. 45350 | Yellow No. 202-2 | | Acid Yellow 73 |
| C.I. 45370 | Orange No. 201 | D & C Orange No. 5 | Solv. Red 72 |
| C.I. 45380 | Red No. 223 | D & C Red No. 21 | Solv. Red 43 |
| C.I. 45380 | Red No. 230-1 | D & C Red No. 22 | Acid Red 87 |
| C.I. 45380 | Red No. 230-2 | | Acid Red 87 |
| C.I. 45410 | Red No. 104-1 | D & C Red No. 28 | Acid Red 92 |
| C.I. 45410 | Red No. 218 | D & C Red No. 27 | Solv. Red 48 |
| C.I. 45410 | Red No. 231 | | Acid Red 92 |
| C.I. 45425 | Orange No. 206 | D & C Orange No. 10 | Solv. Red 73 |
| C.I. 45425 | Orange No. 207 | D & C Orange No. 11 | Acid Red 95 |
| C.I. 45430 | Red No. 3 | FD & C Red No. 3 | Acid Red 51 |
| C.I. 45440 | Red No. 105-1 | | Acid Red 94 |
| C.I. 45440 | Red No. 232 | | Acid Red 94 |
| C.I. 47000 | Yellow No. 204 | D & C Yellow No. 11 | Solv. Yellow 33 |
| C.I. 47005 | Yellow No. 203 | D & C Yellow No. 10 | Acid Yellow 3 |
| C.I. 59040 | Green No. 204 | D & C Green No. 8 | Solv. Green 7 |
| C.I. 60730 | Violet No. 401 | (EXT. D & C Violet No. 2) | Acid Violet No. 43 |
| C.I. 61570 | Green No. 201 | D & C Green No. 5 | Acid Green 25 |
| C.I. 73015 | Blue No. 2 | FD & C Blue No. 2 | Acid Blue 74 |

Parenthetic FDA-No.: Not permitted at present

Other representative examples of water-soluble colorants that are usable in the context of the present invention include, for example, natural coloring materials such as, but not limited to, kuchinashi blue, kuchinashi yellow, shisonin, grape-skin extract, cacao pigment, safflower yellow, hibiscus pigment, lac dye, cochineal, shikon, beet red, brazilin curcumin, riboflavin, lutein, carotenoids, annatto), paprika, carminic acid, carmin, anthocyanins, cabbage, chlorophyll, chlorophyllin, copper-chlorophyll, copper-chlorophyllin, caramel and carbomedicinalis.

However, other colorants such as, for example, near IR dyes, UV dyes, phosphorescent dyes, chemiluminescent compositions and fluorescent compounds, can also be efficiently encapsulated according to the present invention.

Particularly useful are leachless sol-gel particles encapsulating water-soluble fluorescent colorants. Such encapsulated fluorescent colorants can be advantageously used in a myriad of applications, including, for example, cosmetic products such as make-up, eye shadows, lipsticks, lacquers, and the like, as diagnostic agents in in vivo and ex vivo diagnostic applications, and in non-human applications such as, for example, ink compositions, paints, detergents, coatings and packaging materials, as is further detailed hereinbelow.

Representative examples of fluorescent dyes that are usable in the context of the present invention include, without limitation, Rhodamine B, Fluorescein, Pyranine, erythrosine B, eosin Y, Rose Bengal B, Rhodamine 6G, Rose Bengal B, Rhodamine 6G, uranine, Phloxine B and Texas Red. Additional Examples include, without limitation, known fluorescent compounds such as coumarine, pyrene, perylene, anthracene and derivatives thereof, as well as FITC modified polymers (e.g., Fluorescein isothiocyanates), and BODIPY (as used in Molecular Probes).

Representative examples of near IR dyes that are usable in the context of the present invention include, without limitation, squarines, croconines, polymethines, and various metal complexes.

Representative examples of chemiluminescent compositions that are usable in the context of the present invention include, without limitation, compositions containing one or more of luminol, oxalate diesters, hydrogen peroxide, luciferase, dioxetanes and glyoxal.

As is discussed hereinabove, the method according to this aspect of the present invention involves two stages. In the first stage, an inner phase is emulsified in an outer phase that contains a dispersing medium, such that spherical sol-gel particles are formed at the interface by hydrolysis and condensation. Such a process can involve either an aqueous inner phase and a hydrophobic outer phase, so as to form a water-in-oil emulsion, or a hydrophobic inner phase and an aqueous outer phase, so as to form an oil-in-water emulsion. Alternatively, the process can include any two phases that are insoluble one in the other, without having absolute hydrophilic/hydrophobic characters.

The inner phase, according to the present invention, includes one or more of the agent(s) described hereinabove and one or more first sol-gel precursor(s), as is detailed hereinbelow.

As preferred agents according to the present invention are water-soluble agents, the inner phase is preferably water miscible and preferably further includes a water miscible solvent in which the agent is dissolved.

The water miscible solvent may further include an acid or a base, to be used as a catalyst of the sol-gel process. As acid catalysis was found to be more effective for obtaining leachless particles, the inner phase preferably includes an acidic solvent, such as, for example, a solution of various concentrations of acetic acid or any other acid in water.

Further preferably, the inner phase further includes one or more surfactant(s).

The surfactant can be any anionic surfactant, cationic surfactant, amphoteric surfactant, nonionic surfactant or mixtures thereof.

Representative examples of surfactants that are usable in the context of the present invention include, without limitation, Polysorbate 20, Polysorbate 40, Polysorbate 60, Polysorbate 65, Polysorbate 80, Polysorbate 85, Sorbitan laurate, Sorbitan palmitate, Sorbitan stearate, Sorbitan tristearate, Sorbitan oleate, Sorbitan sesquioleate, trioleate Sorbitan, Simulsol 988/989 (PEG-7 Hydrogenated Castor oil), PEG-35-Castor oil, PEG-40-Castor oil, PEG-25-Hydrogenated Castor oil, PEG-40-Hydrogenated Castor oil, PEG-60-Hydrogenated Castor oil, Mix sorbitan ester, Lecithin, sodium oleate and poloxamers.

The outer phase includes a dispersing medium, in which the inner phase, and particularly the agent to be encapsulated, is insoluble. Again, as the agent is preferably water-soluble, the dispersing medium is preferably hydrophobic.

Representative examples of preferred dispersing media that are usable in the context of the present invention include, without limitation, organic solvents such as decanol, castor oil, oleic acid, hexane, acetone, THF, chloroform, dichloromethane, dimethylformamide, diethyl ether, tetrachloromethane, as well as other organic solvents such as esters, ketones, aldehydes, nitrites and the like, or mixtures thereof Alternatively, the dispersing medium can include oils such as, for example, triglycerides, paraffin oil, silicon oil and combinations thereof.

The nature of the outer phase as a whole and of the dispersing medium in particular affects the characteristics of the particles that are formed at the interface of the two phases. For example, as is demonstrated in Example 14 in the Examples section that follows, in the absence of a dispersing medium, the particles are formed as clusters, which are evidently characterized by larger particles size as well as non-uniformity.

Further preferably, the outer phase further includes one or more oil miscible solvents(s) and one or more surfactant(s).

The oil miscible solvent can be, for example, castor oil, oleic acid, decanol, octanol, heptanol, nonanol, linoleic acid, ethyl linoleate, alpha linolenic acid, gamma linolenic acid, stearidonic acid, neuronic acid, palm oil, corn oil, coconut oil, kernel oil, sesame oil, cottonseed oil, safflower oil, flaxseed oil, amber oil, soybean oil, olive oil, almond oil, peanut oil, aniseed oil, bay oil, bergamot oil, cajeput oil, camphor oil, capsicum oleoresin, caraway oil, cardamom oil, cassia oil, cedarwood oil, cinnamon oil, citronnela oil, clove bud oil, clove oil, copaiba balsam oil, coriander oil, cumin seed oil, dill oil, eucalyptus oil, fennel oil, geranium oil, ginger oleoresine, juniperberry oil, lavender oil, lemon oil, methyl salicylate, neroli oil, peppermint oil, pine oil, rosemary oil, spearmint oil, thyme oil red/white, tolu balsam, turpentine oil, castor oil, Cremophor EL (polyethoxylated castor oil surfactant), mono, di and tree glycerides of sorbitan tristearate, lauric acid, citric acid, lactic acid, glyceryl, linoleate, soy oil, edible fats, capric, caprlic, oleyl alcohol, erucic ester, vegetable fats, and ethyl oleate.

Additional oils that can be utilized include mineral oils or lipoids such as, for example, n-hexadecane, 1-hexadecane, cetylic alcohol, palmitic acid, cetylpalmitate, isopripylmyristate, oleum ricini, oleum arachidis, cera perliquida, and paraffinum perliquidum, lauromagrogols, non-oxynols, octoxynoles and poloxamers, as well as polyethylene glycol (PEG) formulations and its alcohol derivatives such as oleyl alcohol, and its analogs, PEG-35-Castor oil, PEG-40-Castor oil, PEG-25-Hydrogenated Castor oil, PEG-40-Hydrogenated Castor oil and PEG-60-Hydrogenated Castor oil.

The surfactant in the outer phase can be any one of the surfactants described hereinabove in the context of the inner phase. However, it was found that using a combination of surfactants in which two different surfactants, having a high and a low HLB value, are each present either in the inner phase or the outer phase, provide for better results and is hence preferable. Representative examples of such a combination include, without limitation, sorbitan oleate or sorbitan sesquioleate and polysorbate 80, trioleate sorbitan and polysorbate 85 and sorbitan stearate and polysorbate 60.

The outer phase preferably further includes one or more viscosity modifying agent(s). The addition of a viscosity modifying agent, which is also referred to herein as a thickener, enables to control the viscosity of the dispersing medium and enhances the stability of the emulsion, and thus provides for higher yield of the obtained particles. Furthermore, adding a viscosity modifying agent enables to reduce the amount of the dispersing medium. As preferred dispersing media typically include organic solvents, using large amounts thereof typically imposes technical limitations, such as cost, hazardousness, toxicity and waste disposal, and therefore reducing the amount of the dispersing medium is highly desirable.

As is demonstrated in the Examples section that follows (Examples 8-11), the substantially leachless, colorant-encapsulating sol-gel particles of the present invention were successfully obtained when various viscosity modifying agents, such as hydroxypropyl cellulose and ethyl cellulose, were used. Other viscosity modifying agents which can be utilized according to the present invention include, without limitation, other celluloses such as, for example, hydroxypropyl methyl cellulose, methyl cellulose, hydroxyethyl cellulose and the like, acrylates such as, for example, salcare-sodium acrylate copolymer, paraffinium liquidum and PPG-1 trideceth-6, as well as PVP, maltodextrin, xantham gum, carbomers, lechitins, guar gum and wax.

In addition to the surfactants and thickeners described hereinabove, other agents, which may affect the properties of the emulsion and hence the characteristics of the formed particles, can be added to the inner and/or outer phases at various stages of this method of the present invention. Such agents include, for example, emulsifiers, stabilizers, other thickeners and gelling agents.

Representative examples of such agents include, without limitation, Lecithins, Alginic acid, Sodium alginate, Potassium alginate, Ammonium alginate, Calcium alginate, Propane-1,2-diol alginate, Agar, Carrageenan, Processed eucheuma seaweed, Locust bean gum, carob gum, Guar gum, Tragacanth, Acacia gum, gum arabic, Xanthan gum, Karaya gum, Tara gum, Gellan gum, Konjac, Polyoxyethylene sorbitan monolaurate, Polyoxyethylene sorbitan mono-oleate, Polyoxyethylene sorbitan monopalmitate, Polyoxyethylene sorbitan monostearate, Polyoxyethylene sorbitan tristearate, Pectins, Ammonium phosphatides, Sucrose acetate isobutyrate, Glycerol esters of wood resins, Cellulose, Methyl cellulose, Hydroxypropyl cellulos, Hydroxypropyl methyl cellulose, Ethyl methyl cellulose, Carboxy methyl cellulose, Sodium carboxy methyl cellulose, Crosslinked sodium carboxy methyl cellulose, Enzymatically hydrolysed carboxy methyl cellulose, Sodium, potassium and calcium salts of fatty Acids, Magnesium salts of fatty acids, Mono- and diglycerides of fatty acids, Acetic acid esters of mono- and diglycerides of fatty acids, Lactic acid esters of mono- and diglycerides of fatty acids, Citric acid esters of mono- and diglycerides of fatty acids, Tartaric acid esters of mono- and diglycerides of fatty acids, Mono- and diacetyltartaric acid esters of mono- and diglycerides of fatty acids, Mixed acetic and tartaric acid esters of mono- and diglycerides of fatty acids, Sucrose esters of fatty acids, Sucroglycerides, Polyglycerol esters of fatty acids, Polyglycerol polyricinoleate, Propane-1,2-diol esters of fatty acids, Thermally oxidized soy bean oil interacted with mono and diglycerides of fatty acids, Sodium stearoyl-2-lactylate, Calcium stearoyl-2-lactylate, Stearyl tartrate, Sorbitan monostearate, Sorbitan tristearate, Sorbitan monolaurate, Sorbitan monooleate, Sorbitan monopalmitate and Invertase.

Other agents which can similarly be beneficially used in preparing the sol-gel particles of the present invention include, for example, acidity regulators, anti-caking agents, anti-foaming agents, bulking agents, carriers and carriers solvents, emulsifying salts, firming agents, flavor enhancers; flour treatment agents, foaming agents, glazing agents, humectants, modified starches, packaging gases, propellants, raising agents and sequestrants.

Representative examples of such agents include, without limitation, Calcium carbonates, Acetic acid, Potassium acetate, Sodium acetate, Calcium acetate, Lactic acid, Carbon dioxide, Malic acid, Fumaric acid, Sodium lactate, Potassium lactate, Calcium lactate, Citric acid, Sodium citrates, Potassium citrates, Calcium citrates, Tartaric acid (L-(+)), Sodium tartrates, Potassium tartrates, Sodium potassium tartrate, Phosphoric acid, Sodium phosphates, Potassium phosphates, Calcium phosphates, Magnesium phosphates, Sodium malates, Potassium malate, Calcium malates, Metatartaric acid, Calcium tartrate, Adipic acid, Sodium adipate, Potassium adipate, Succinic acid, Triammonium citrate, Calcium disodium ethylene diamine tetra-acetate (calcium disodium EDTA), Glycerol, Polyoxyethylene (40) stearate, Diphosphates, Triphosphates, Polyphosphates, Beta-cyclodextrin, Sodium carbonates, Potassium carbonates, Ammonium carbonates, Magnesium carbonates, Hydrochloric acid, Potassium chloride, Calcium chloride, Magnesium chloride, Stannous chloride, Sulphuric acid, Sodium sulphates, Potassium sulphates, Calcium sulphate, Ammonium sulphate, Aluminium sulphate, Aluminium sodium sulphate, Aluminium potassium sulphate, Aluminium ammonium sulphate, Sodium hydroxide, Potassium hydroxide, Calcium hydroxide, Ammonium hydroxide, Magnesium hydroxide, Calcium oxide, Magnesium oxide, Sodium ferrocyanide, Potassium ferrocyanide, Calcium ferrocyanide, Sodium aluminium phosphate, Silicon dioxide, Calcium silicate, Magnesium silicate, Magnesium trisilicate, Talc, Sodium aluminium silicate, Potassium aluminium silicate, Aluminium calcium silicate, Bentonite, Aluminium silicate (Kaolin), Fatty acids, Gluconic acid, Glucono delta-lactone, Sodium gluconate, Potassium gluconate, Calcium gluconate, Ferrous gluconate, Ferrous lactate, Glutamic acid, Monosodium glutamate, Monopotassium glutamate, Calcium diglutamate, Monoammonium glutamate, Magnesium diglutamate, Guanylic acid, Disodium guanylate, Dipotassium guanylate, Calcium guanylate, Inosinic acid, Disodium inosinate, Dipotassium inosinate, Calcium inosinate, Calcium 5'-ribonucleotides, Disodium 5'-ribonucleotides, Glycine and its sodium salt, Zinc acetate, Dimethylpolysiloxane, Beeswax, white and yellow, Candelilla wax, Carnauba wax, Shellac, Microcrystalline wax, Montan acid esters, Oxidised Polyethylene wax, L-Cysteine, Carbamide, Quillaia extract, Polydextrose, Polyvinylpyrrolidone, Polyvinylpolypyrrolidone, Oxidised starch, Monostarch phosphate, Distarch phosphate, Phosphated distarch phosphate, Acetylated starch, Acetylated Starch, Acetylated distarch adipate, Hydroxyl propyl starch, Hydroxy propyl distarch phosphate, Starch sodium octenyl succinate, Acetylated oxidised starch, Polyethylene glycol 6000, Triethyl citrate, Glyceryl triacetate (triacetin) and Propan-1,2-diol (propylene glycol).

In a preferred embodiment of the method of the present invention, the first stage of the method involves dissolving a water-soluble agent in a water miscible solvent, which preferably further includes an acid, in the presence of one or more surfactant(s), and thereafter adding a first sol-gel precursor, so as to produce an inner phase. The inner phase is thereafter emulsified in an oil miscible solvent, preferably in the presence of a second, different surfactant, as is described hereinabove, so as to form an emulsion, which is added into a hydrophobic dispersing medium that optionally further includes one or more viscosity modifying agent(s) and/or other surface active agents as detailed hereinabove. Spherical initial sol-gel particles encapsulating the agent are thus formed by hydrolysis and polycondensation of the sol-gel precursor at the interface of the two phases.

As is demonstrated in the Examples section that follows, the initial sol-gel particles obtained in the first stage of the method of the present invention have a relatively small average particle size, which ranges between 0.05 micron and 2 microns and, more specifically, between about 1.3 microns and about 1.4 microns.

As used herein the term "about" refers to ±10%.

The initial sol-gel particles of the present invention are further characterized by a surface area of between about 1 $m^2$/gram and about 5 $m^2$/gram and, more specifically, between about 2 $m^2$/gram and 3 $m^2$/gram. Such a surface area is relatively low as compared with typical sol-gel particles.

However, although characterized by small particles size and low surface area, the initial sol-gel particles of the present invention have been found to be inefficient in preventing leaching of substantial amount of an encapsulated water-soluble agent. In an extraction assay that has been conducted, as is detailed in the Examples section that follows, more than 3% of the agent has been extracted after only 25 hours of mixing and agitating the particles in an aqueous extraction medium.

This assay further demonstrates the need for an improved method of producing leachless sol-gel particles, which is answered by the second stage of the method of the present invention.

In the second stage, the initial sol-gel particles are reacted with a second sol-gel precursor. This stage is preferably preformed by suspending the initial sol-gel particles in a second sol-gel precursor and thereafter adding an acidic or basic catalyst, so as to activate the hydrolysis and condensation of the sol-gel precursor. The catalyst is preferably an acid.

The first and second sol-gel precursors used in the method of the present invention can be the same or different. Each of the sol-gel precursors can be, for example, a metal alkoxide monomer, a semi-metal alkoxide monomer, a metal ester monomer, a semi-metal ester monomer, a silazane monomer, a monomer having the formula $M(R)_n(P)_m$, whereas M is a metal or a semi metal, R is a hydrolyzable substituent, n is an integer from 2 to 6, P is a non-polymerizable substituent and m is and integer from 0 to 6, a partially hydrolyzed polymer thereof, a partially condensed polymer thereof and a combination thereof.

The metal can be, for example, Si, Ti, Zr, Ni, Al and Zn. Preferably, the first and the second sol-gel precursors include inorganic silica monomers such as, for example, tetraalkoxysilanes (e.g., tetramethoxysilane, tetraethoxysilane, etc.) or organically-modified silica monomers having the formula $M(R)_n(P)_m$ described hereinabove, where M is Si.

Further preferably, the first sol-gel precursor is a water-soluble monomer having the formula $M(R)_n(L)_m$, where M is a metal or a semi metal as is described hereinabove, R is a hydrolyzable substituent, n is an integer from 2 to 6, L is a hydrolyzable water-soluble substituent and m is and integer from 1 to 6, preferably from 1 to 4, and more preferably from 2 to 3. The use of such a water-soluble monomer provides for an inner phase that is characterized by enhanced hydrophilic nature and hence enhances the emulsion stability.

The water-soluble substituents L can be, for example, glycol, glycol ester, glycerol, sugar and derivatives thereof (see, for example, I. Gill, A. Ballesteros, J. Am. Chem. Soc. 120, 1998, 8587).

As is further demonstrated in Examples 3 and 4 in Examples section that follows, the agent-encapsulating sol-gel particles obtained as described hereinabove, were found to be substantially leachless, particularly as compared with the initial sol-gel particles described hereinabove. In a prolonged extraction assay, which was conducted using an aqueous medium containing strong extracting reagents such as SLS and sodium fluoride, less than 1.5% of the encapsulated colorant leached into the extraction medium after mixing and agitating the particles in the extraction medium for a month at 40° C.

The substantially leachless particles obtained by the method of the present invention are further characterized by a small particles size that ranges between about 0.05 micron and 5 microns, preferably between 0.05 micron and 2 microns, and by a surface area that ranges between about 0.01 m²/gram and 5 m²/gram, preferably between about 0.01 m²/gram and 1 m²/gram.

The substantially leachless particles of the present invention are further characterized as spherical and transparent particles.

Hence, according to another aspect of the present invention there are provided substantially leachless, transparent, agent-encapsulating sol-gel particles having a spherical shape, an average particles size that ranges between 0.05 micron and 5 microns in diameter and a surface area that ranges between 0.01 m²/gram and 5 m²/gram, which are prepared as described hereinabove.

Further according to the present invention there are provided substantially leachless, transparent, agent-encapsulating sol-gel particles, that are characterized by leaching of no more than 2 weight percentages of the agent upon mixing and agitating the sol-gel particles with an extraction medium for at least 7 days at 40° C.

The agent encapsulated in the sol-gel particles of the present invention can be any of the agents described hereinabove.

However, as the substantially leachless sol-gel particles of the present invention are characterized by small particles size, spherical shape and hence non-grittiness and transparency, and are preferably composed of non-toxic components (e.g., silica), they are particularly useful as substantially leachless colorant-encapsulating particles, which may be used in colored cosmetic, oral care and food products.

Hence, according to another aspect of the present invention, there is provided a colored cosmetic product stable to color leaching and/or migration, which comprises the substantially leachless, colorant-encapsulating sol-gel particles of the present invention and a cosmetically acceptable carrier, whereby after storage, substantially no significant amount of the colorant is observable as migrating into the carrier.

Further according to the present invention there is provided a method of preparing the colored cosmetic product of the present invention. The method is effected by preparing the substantially leachless, colorant-encapsulating sol-gel particles of the present invention, as is detailed hereinabove, and mixing the colorant-encapsulating sol-gel particles with a cosmetically acceptable carrier.

Examples of acceptable carriers that are useful in the context of the present invention include, without limitation, emulsions, creams, aqueous solutions, oils, ointments, pastes, gels, lotions, milks, foams, suspensions and powders.

The acceptable carrier of the present invention may include, for example, a thickener, an emollient, an emulsifier, a humectant, a surfactant, a suspending agent, a film forming agent, a foam building agent, a preservative, an antifoaming agent, a fragrance, a lower monoalcoholic polyol, a high boiling point solvent, a propellant, a colorant, a pigment or mixtures thereof.

Therefore, the colored cosmetic product of the present invention can be in the form of an emulsion, a cream, an aqueous solution, an oil, an ointment, a paste, a gel, a lotion, a milk, a suspension, a powder, a foam, a shampoo, a hair conditioner, a lacquer, a makeup and a solid stick and hence include cosmetic products such as, but not limited to, a lipstick, an eye shadow, a blush, a lacquer, a lipstick, an eye shadow, a blush, a lacquer, a glitter, a shower gel, an oral care product (e.g., a dentifrice), a lip gloss, a cream, a soap, a mascara, a shampoo and an anti-aging product.

The colored cosmetic products of the present invention are highly advantageous since (i) the substantially leachless colorant encapsulating sol-gel capsules are characterized by all the properties that render a colored cosmetic product beneficial, as is discussed hereinabove; (ii) the encapsulation of the colorant in the leachless sol-gel particles of the present invention allows the use of non-FD&C colors, since the contact of the colorant with the skin is avoided; and (iii) the use of the leachless sol-gel capsules of the present invention allows the use of any cosmetically acceptable carrier and further allows the use of any other component in the formulation, regardless of its reactivity toward the encapsulated colorant.

The sol-gel particles of the present invention are particularly advantageous for use is colored dentifrices. As is discussed in detail hereinabove, the presently known methods of producing multicolored dentifrices such as striped or speckled dentifrices are limited by substantial leaching of the colorant(s) into the surrounding medium. As is described in the Examples section that follows (Example 4), the non-leachable nature of the colorant-encapsulating sol-gel particles of the present invention was demonstrated in an extraction assay that included a typical dentifrice medium, which contained reagents such as sodium lauryl sulfate and sodium fluoride.

Hence, according to another aspect of the present invention, there is provided a multicolored dentifrice composition, which is stable to color bleeding. The multicolored dentifrice composition of the present invention comprises a plurality of components which include at least one component that contain the substantially leachless, colorant-encapsulating sol-gel particles of the present invention, whereby after storage, substantially no significant amount of the colorant is observable as migrating into any other dentifrice component.

The multicolored dentifrice composition of the present invention can thus be either a striped composition or a speckled composition and can include one or more colored components comprised of the sol-gel particles of the present invention, such that in each component the sol-gel particles encapsulate a different colorant.

Further according to the present invention there is provided a method of preparing the multicolored dentifrice composition of the present invention. The method is effected by preparing a plurality of different colored dentifrice components that are in physical interfacial contact therebetween, whereby one or more of these components contains the substantially leachless, colorant-encapsulating sol-gel particles of the present invention, prepared as described hereinabove.

In other words, the method according to this aspect of the present invention is effected by preparing one or more types of the sol-gel particles of the present invention, as is detailed hereinabove, whereby each type encapsulates a different colorant and thereafter align the sol-gel particles to be in physical interfacial contact therebetween. Alternatively, the method can be effected by preparing one dentifrice component that includes the colorant encapsulating sol-gel particles of the present invention, preparing other colored or non-colored dentifrice components and thereafter align the components to be in physical interfacial contact therebetween.

According to another aspect of the present invention, there is provided a colored food additive that is stable to color leaching and/or migration. The colored food additive of the present invention comprises the substantially leachless, colorant-encapsulating sol-gel particles of the present invention and an edible carrier, whereby after storage, substantially no significant amount of the colorant is observable as migrating into the carrier.

The phrase "food additive" [defined by the FDA in 21 C.F.R. 170.3(e)(1)] includes any liquid or solid material intended to be added to a food product. This material can, for example, include an agent having a distinct taste, color and/or flavor or physiological effect (e.g., vitamins).

The food additive composition of the present invention can be added to a variety of food products.

As used herein, the phrase "food product" describes a material consisting essentially of protein, carbohydrate and/or fat, which is used in the body of an organism to sustain growth, repair and vital processes and to furnish energy. Food products may also contain supplementary substances such as minerals, vitamins and condiments. See Merriani-Webster's Collegiate Dictionary, 10th Edition, 1993.

The colored food additives of the present invention can therefore be used to provide a colored appearance to food products such as, for example, candies, powdered food products, preserved food products and the like. The encapsulation of the colorant in the leachless sol-gel particles of the present invention is highly advantageous since it involves a non-toxic encapsulation matrix and provides for stable and powerful appearance of the colored product.

As is discussed hereinabove, the substantially leachless, agent-encapsulating and particularly colorant-encapsulating sol-gel particles of the present invention may also be utilized in preparing other products such as, for example, colored pharmaceutical products (e.g., colored drugs), colored detergents, colored antiperspirants, ink compositions, colored packaging materials, colored coatings, diagnostic products in which fluorescent compounds or radioactive agents are encapsulated and products that contain particles encapsulating near IR dyes, which can be used in the various applications described hereinabove.

Hence, according to another aspect of the present invention, there is provided a colored article-of-manufacture that is stable to color leaching and/or migration. The colored article-of-manufacture of the present invention comprises the substantially leachless, colorant-encapsulating sol-gel particles of the present invention and a suitable carrier, whereby after storage, substantially no significant amount of the colorant is observable as migrating into the carrier.

The article-of-manufacture can be, for example, a cosmetic product, an oral care product and a food product, as is described in detail hereinabove, and can further be, for example, a pharmaceutical product, a diagnostic agent, a detergent, an ink composition, an antiperspirant, a paint, a coating, a packaging material, a cloth, a plastic or any other article-of-manufacture in which encapsulation of a colorant in non-toxic, non-leachable matrix, such as the leachless sol-gel particles of the present invention, is beneficial.

For example, solid-like cosmetic products such as make-up, eye shadows, lipsticks and lacquers typically include colorants such as fluorescent dyes. Although such products are typically formulated in non-aqueous carriers, and are therefore devoid of migration of water-soluble colorants into the carrier, their contact with the skin should be avoided, due to the toxicity of the fluorescent dyes, and therefore their encapsulation in the leachless sol-gel particles of the present invention is highly advantageous.

Pharmaceutical products such as, for example, drugs formulated as color-coated tablets, which include the leachless, colorant-encapsulating sol-gel particles of the present invention are also highly beneficial. Such products include a non-toxic, biodegradable coating and provide for a solid and colorful appearance of the product, which remains intact under conditions such as humidity, heat and contact with different substances.

Diagnostic agents, which include leachless sol-gel particles of the present invention, encapsulating, for example, fluorescent dyes, can be beneficially used in ex-vivo and in-vivo applications. In in-vivo applications, the encapsulation of the fluorescent dye in the leachless sol-gel particles of the present invention is highly advantageous since it avoids the contact of the fluorescent dye with organs in the human body, whereby in ex-vivo applications, such an encapsulations avoids the contact of the fluorescent dye with other components in the tested samples.

Detergents, e.g., for laundry and dishwashing applications, including the leachless colorant-encapsulating sol-gel particles of the present invention are highly advantageous since water-soluble colorants can be safely included in the detergents, without causing any damage to, for example, the washing machine or the dishwasher.

Similarly, ink compositions, antiperspirants, paints (e.g., car paints and wall paints), coatings (for, e.g., textiles, shoes, toys, wood products, papers, marble and plastics) and packaging materials can beneficially include the leachless sol-gel particles of the present invention, encapsulating water-soluble, toxic and/or chemically reactive colorants (e.g., fluorescent and/or near IR dyes), as is detailed hereinabove.

In colored articles-of manufacture such as, for example, plastics, cloths, papers, marbles, toys (e.g., light sticks), the leachless sol-gel particles of the present invention can be also incorporated within the article-of-manufacture, without affecting other components in the article-of-manufacture.

Hence, as is demonstrated in the Examples section that follows (see, Example 22 and FIG. 3), the leachless agent-encapsulating sol-gel particles of the present invention can be advantageously incorporated in plastics (e.g., polyethylene, polycarbonates and the like), by compounding, with no apparent damage neither to the sol-gel particles nor for the plastic. Incorporation of pigments in thermoplastics is known to cause detrimental effects on the physical and mechanical properties of thermoplastics (see, for example, Parikh et al., Mater. Eng. (Cleveland), 98(1), 37-40 (English) 19830, and therefore encapsulation thereof in the leachless particles of the present invention advantageously abolishes these effects.

The suitable carrier is selected to fit the intended application of the article-of-manufacture.

The article-of-manufactures of the present invention can be produced using the method described hereinabove for preparing the substantially leachless, agent-encapsulating sol-gel particles of the present invention and incorporating these particles within the final product, using known techniques.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Preparation of Colored Silica Microparticles

The water-soluble dye FD&C Blue No. 1 (0.002-0.2 gram) and Polysorbate 80 (0.01-1 gram) were dissolved in a solution of 30-70% acetic acid in water (10-40 grams). 10-40 grams tetraethyl orthosilicate (TEOS) were then added and the obtained solution was stirred at room temperature. The solution was emulsified in a stirred, cooled oil phase containing 5-15 grams Sorbitan Oleate and 100-300 grams castor oil. The obtained emulsion was poured into 100-800 grams decanol and the obtained mixture was stirred using a mechanical stirrer. A fine particulate powder was thus obtained and was collected by sedimentation in a centrifuge. The precipitate was washed consecutively with hexane, ethanol and hexane, and was dried in an oven.

Example 2

Preparation of Coated Colored Silica Microparticles 1-10 grams of the dry powder obtained in Example 1 were suspended in 40 grams TEOS and the mixture was stirred at room temperature. 0.01-5N HCl (50-500 µl) was then added to the stirred dispersion. The obtained powder was separated as described hereinabove (in Example 1), and the precipitate was consecutively washed with hexane, ethanol, NaOH-containing ethanol, sodium lauryl sulfate solution (SLS), water and ethanol. The obtained particles were then dried in an oven.

Example 3

Qualitative Leaching Measurements of the Coated Colored Silica Particles

The coated colored silica particles obtained in Example 2 were qualitatively tested for dye migration into various organic and inorganic media, by shaking the particles in the extraction medium at room temperature and observing coloration of the media thereafter.

This extraction test was performed with the following organic media: acetone, ethanol, methanol, decanol, THF, TEOS, dichloromethane, flavor oil, isopropyl alcohol, DMSO, triethanolamine, DMF and diethyl ether, Similarly, the extraction test was performed with the following inorganic media: water, 3% SLS, 0.1N Na OH, 1% sodium saccharin, 0.01-5N HCl, 1% sodium fluoride, 1% NaCl, 70% sorbitol, 2% urea, 30-70% acetic acid, 90% lactic acid and 0.1% citric acid.

Example 4

Comparative Characterization of the Coated and Uncoated Colored Silica Particles A series of tests have been conducted in order to determine and compare the physical properties of the uncoated and coated colored silica particles obtained in Example 1 and Example 2, respectively. Two sets of particles, denoted as Example 2a and Example 2b in Table 1 below, were prepared according to Example 2. The analytical methods are set forth hereinunder and the results are summarized in Table 2 below.

FD&C Blue No. 1 concentration: Fifty (50) mg of colored silica particles were placed in a plastic beaker, 3 ml of 3% hydrofluoric acid in water were added thereto and the solution was stirred until dissolution of the silica has been observed (after about 5 minutes). The solution was neutralized by careful, slow addition, of about 17 ml 1% sodium carbonate solution. The dissolved sample was transferred quantitatively into a 50 ml volumetric flask, which was filled with water. The absorption of this sample was measured, using a UV-VIS spectrometer at a maximum of about 629 nm against water, and compared with a standard solution of FD&C Blue No. 1 so as to determine the concentration of the dye in the silica particles.

Dye extraction test: The amount of a dye that migrates from the microspheres into a liquid dentifrice model was determined using an extraction solution consisting of: 2.0 grams Sodium Lauryl Sulfate; 0.3 gram Sodium Saccharin; 0.33 gram Sodium Fluoride; 42.3 grams 70% Sorbitol Solution; 1.0 gram Flavor Oil; and 35 grams Pure Water.

The above solution was freshly prepared and filtered to ensure clarity. Depending on the dye content, 50-500 mg of colored silica particles were placed in a 50 ml volumetric flask, and the flask was filled and mixed with the extraction solution. The sample was further agitated in a thermostatic bath, at 40° C., at 150 stroke/minute. At various, predetermined, time periods a sample was withdrawn from the flask and was filtered through Polypropylene Membrane Syringe Filter and the absorption of the remaining filtered solution was measured using a UV-VIS spectrometer at about 629 nm against a blank solution of filtered extraction solution. The absorption of the extracted dye was compared to that of a standard solution of the dye in water and the concentration of the extracted dye was thereby calculated.

Particles size distribution: Silica samples (about 150 mg) were weighed into a test tube. Two ml methanol were added and the mixture was placed for 5-10 minutes in an ultrasonic bath, to obtain a dispersion of the particles. The obtained dispersion was thereafter added directly into the sample bath of a Malvern Mastersizer 2000 equipped with a Hydro G2000 bath, to give obscuration of 10-20%.

Specific surface area (BET measurements): The specific surface area of the microparticles was measured by $N_2$ gas adsorption/desorption full isotherm on a Micromeritics ASAP 2000 Surface Area Analyzer. The samples were degassed for 1 day at 150° C. prior to measurement. The data was analyzed by BET equation.

Loss of day: The weight loss of the microparticles upon drying was measured in a Mettler Toledo HR73 Halogen Moisture Analyzer.

TABLE 2

| Sample | Dye concentration (% wt/wt) | Extraction (wt % of total dye) | Particles size [d (0.9)] | BET ($m^2$/gr) | Loss on dry (% wt/wt) |
| --- | --- | --- | --- | --- | --- |
| Example 1 | 0.4 | 3.53 after 25 h<br>3.80 after 144 h<br>3.86 after 240 h | 1.324 | 2.8 | 6.73 |
| Example 2a | 0.34 | 1.25 after 25 h<br>1.38 after 144 h<br>1.46 after 240 h | 1.320 | 0.2 | 4.11 |
| Example 2b | 0.39 | 1.165 after 25 h<br>1.260 after 96 h<br>1.289 after 200 h<br>1.321 after 270 h<br>1.367 after 28 days | 1.193 | Not determined | Not determined |

The obtained data clearly indicate that while the average particles size and the concentration of the encapsulated dye are the same in both silica particles, the silica particles of Examples 1 and 2 clearly differ one from the other by their encapsulation capability. As is shown in Table 2, the obtained results clearly demonstrate that a significantly lower amount of dye is extractable from the coated silica particles (of Example 2) as compared with the uncoated particles (of Example 1). In accordance with these results, it is further indicated that the measured surface area of the coated silica particles (of Example 2) is lower by an order of magnitude than that of the uncoated particles (of Example 1), and that the ability of the coated particles of Example 2 to adsorb water is lower as compared with the uncoated particles of Example 1.

The data obtained with respect to the surface area of both the coated and uncoated particles is of particular importance. Typical surface area measured for silica microparticles prepared by a sol-gel process ranges between 10 $cm^2$/gram to 1000 $m^2$/gram (*Sol-Gel Science: The Physics and Chemistry of Sol-Gel Processing*, C. Jeffrey Brinker, George W. Scherer, May 1990), and hence the surface area of the uncoated particles of Example 1 is at the very low end of this range. Such a low surface area provides indication of low porosity of the particles. Nevertheless, as is further shown by the obtained data, having such a low surface area does not necessarily provide microparticles that prevent extraction of the dye therefrom. However, preparing the microparticles by the procedure employed in Example 1, followed by coating the particles with a second silica layer as is described in Example 2, provides non-porous, sealed colored microparticles, which are characterized by diminished leaching and migration of the water-soluble dye into water-based formulations.

It should further be noted that based on other comparative experiments conducted, the washing and drying steps in Example 1 are crucial for effective performance of the particles obtained in Example 2. When the particles obtained in Example 1 were not washed prior to the coating step in Example 2, the coated particles obtained in Example 2 were found to be relatively leachable. The protocol described in Example 1 thus provides microparticles having cleaned-up surface and pores and hence allows a faster and more effective penetration of the TEOS used in Example 2 into the particles pore network.

Example 5

Preparation of Colored Uncoated Silica Microparticles Containing Higher Amount of Dye The procedure described in Example 1 was performed, using a high concentration of FD&C Blue No. 1. The microparticles obtained contained 4.5% (wt/wt) dye, while 90% thereof were characterized by particles size smaller than 1.06 micron.

Example 6

Preparation of Colored Coated Silica Microparticles Containing Higher Amount of Dye Similarly, the procedure described in Example 2 was performed, using a high concentration of FD&C Blue No. 1. The microparticles obtained contained 4.4% (wt/wt) dye and were characterized by particles size smaller than 1.06 micron.

Example 7

Figure 1B:
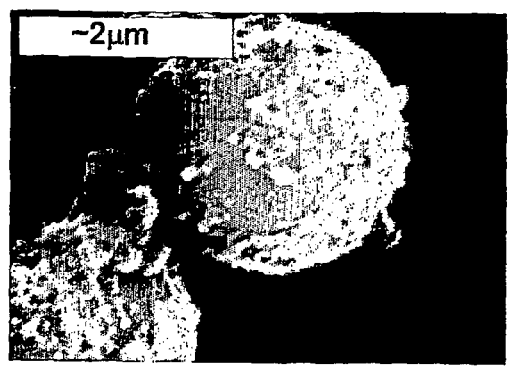

Comparative SEM Study of the Shape and Texture of Coated and Uncoated Colored Silica Microparticles The SEM images of the microparticles obtained in Examples 1, 2, 5 and 6 are presented in FIGS. 1*a*, 1*b*, 2*a-b* and 2*c*, respectively. As is shown in FIG. 1*a*, a typical SEM image of silica particles prepared by a sol-gel process was obtained for the colored microparticles of Example 1, indicating a relatively smooth surface. However, as is shown in FIG. 1*b*, coating the particles with a second silica layer resulted in microparticles having reduced smoothness.

Figure 2A:
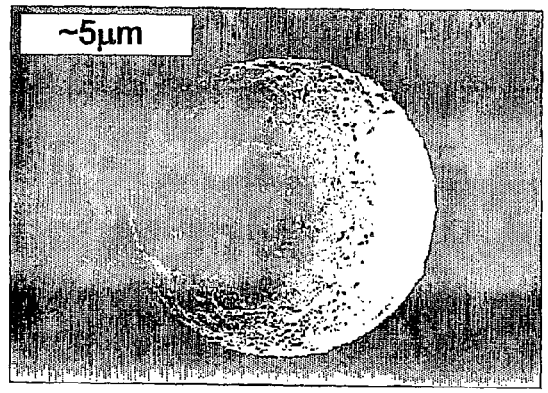
FIGS. 2a-c present SEM images of uncoated (FIGS. 2a and 2b) and coated (FIG. 2c) colored silica microspheres prepared according to another preferred embodiment of the present invention.
Figure 2B:
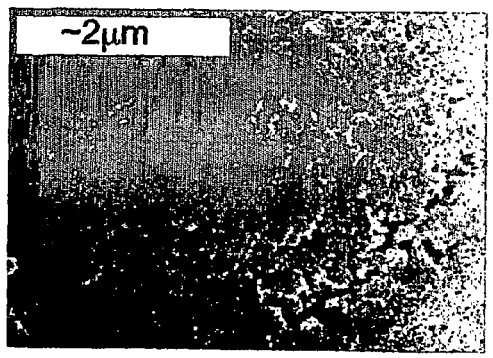
Figure 2C:
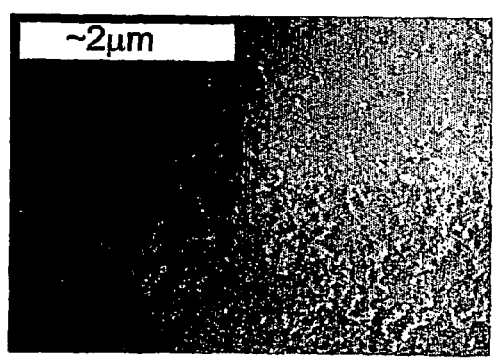

FIG. 2*a* presents typical SEM images of the particles obtained in Example 5 (containing higher amount of the encapsulated dye). However, as is shown in FIG. 2*b*, this process results in formation of cracks on the particles surface, which, as is shown in FIG. 2*c*, are sealed by the second silica layer applied to the particles in Example 6.

Example 8

Preparation of Colored Silica Particles in the Presence of Hydroxypropyl Cellulose

The dye FD&C Blue No. 1 ((0.002-0.2 gram) and Polysorbate 80 (0.01-1 gram) were dissolved in 10-40 grams solution of 30-70% acetic acid in water. 10-40 grams TEOS were then added, the mixture was stirred. The obtained acidic solution was then emulsified in a stirred solution containing 1-10 grams Sorbitan Oleate (Span 80), 1-10 grams Hydroxypropyl Cellulose (HPC) and 50-200 grams Decanol, and the emulsion was stirred using a magnetic or a mechanical stirrer. The product was obtained as a fine particulate powder, which was collected by sedimentation in a centrifuge. The obtained precipitate was washed consecutively with acetone, SLS and hexane, and was dried in an oven.

Example 9

Preparation of Coated Colored Silica Particles Prepared in the Presence of Hydroxypropyl Cellulose

1-10 grams of the dry powder obtained in Example 8 were suspended in 40 grams TEOS or a solution of TEOS and an organic solvent such as, for example, decanol, castor oil or oleic acid, and the mixture was stirred. A catalytic amount of an acid (e.g., 0.01N-5N HCl, 90% lactic acid, 0.1% citric acid, 50% acetic acid) was then added to the stirred dispersion. The obtained powder was separated as described in Example 8, and the obtained precipitate was washed consecutively with acetone, ethanol, NaOH-containing ethanol, SLS solution, water and ethanol. The product was then dried in an oven.

Example 10

Preparation of Colored Silica Particles in the Presence of Ethyl Cellulose

The dye FD&C Blue No. 1 (0.002-0.2 gram) and Polysorbate 80 (0.01-1 gram) were dissolved in 10-40 grams solution of 30-70% acetic acid in water. 10-40 grams TEOS were then added and the mixture was stirred. The obtained acidic solution was then emulsified in a solution containing 1-10 grams Sorbitan Oleate (Span 80), 1-10 grams Ethyl Cellulose (ETC) and 50-200 grams Decanol, and the emulsion was stirred using a magnetic or a mechanical stirrer. The product was obtained as a fine particulate powder, which was collected by sedimentation in a centrifuge. The obtained precipitate was washed consecutively with acetone, SLS and hexane, and was dried in an oven.

Example 11

Preparation of Coated Colored Silica Particles Prepared in the Presence of Ethyl Cellulose

1-10 grams of the dry powder obtained in Example 10 were suspended in 40 grams TEOS or a solution of TEOS and an organic solvent such as, for example, decanol, castor oil or oleic acid, and the mixture was stirred at room temperature. A catalytic amount of an acid (e.g., 0.01-5N HCl, 90% lactic acid, 0.1% citric acid, 30-70% acetic acid) was then added to the stirred dispersion. The obtained powder was separated as described in Example 8, and the obtained precipitate was washed consecutively with acetone, ethanol, NaOH-containing ethanol, SLS solution, water and ethanol. The product was then dried in an oven.

Example 12

Preparation of Colored Silica Microparticles in the Presence of Sunflower Oil

The water-soluble dye FD&C Blue No. 1 (0.002-0.2 gram) and Polysorbate 80 (0.01-1 gram) were dissolved in a solution of 30-70% acetic acid in water (10-40 grams). 10-40 grams tetraethyl orthosilicate (TEOS) were then added and the obtained solution was stirred. The solution was thereafter cooled and was emulsified in a stirred, cooled oil phase containing 5-15 grams Sorbitan Oleate and 100-300 grams sunflower oil. The obtained emulsion was poured into 100-800 grams decanol and the mixture was stirred using a mechanical stirrer. A powder was thus obtained and was collected by sedimentation in a centrifuge. The precipitate was washed consecutively with hexane, ethanol and hexane, and was dried in an oven.

Example 13

Preparation of Coated Colored Silica Microparticles in the Presence of Sunflower Oil

1-10 grams of the dry powder obtained in Example 12 were suspended in 40 grams TEOS and the mixture was stirred. 0.01-5N HCl (50-500 µl) was then added to the stirred dispersion and mixing was continued. The obtained powder was separated as described hereinabove (in Example 1), and the precipitate was consecutively washed with hexane, ethanol, NaOH-containing ethanol, sodium lauryl sulfate solution (SLS), water and ethanol. The obtained particles were then dried in an oven.

Example 14

Preparation of Colored Silica Microparticles in the Absence of a Dispersing Medium

The water-soluble dye FD&C Blue No. 1 (0.002-0.2 gram) and Polysorbate 80 (0.01-1 grain) were dissolved in a solution of 30-70% acetic acid in water (10-40 grams). 10-40 grams tetraethyl orthosilicate (TEOS) were then added and the obtained solution was stirred. The solution was thereafter emulsified in a stirred, cooled oil phase containing 5-15 grams Sorbitan Oleate and 100-300 grams sunflower oil. The obtained mixture was poured into 100-800 grams sunflower oil and stirred using a mechanical stirrer. A powder was thus obtained and was collected by sedimentation in a centrifuge. The precipitate was washed consecutively with hexane, ethanol and hexane, and was dried in an oven. The product was obtained as clusters having a size greater than 10 microns.

Example 15

Preparation of Coated and Uncoated Colored Silica Microparticles

Uncoated and coated colored microparticles encapsulating FD&C Red No. 40 were prepared according to the procedures described in Examples 1 and 2, respectively. The dye concentration in the resulting microparticles was 3.54% (wt/wt) and 90% of the microparticles were characterized by particles size smaller than 1.05 micron.

Example 16

Preparation of Coated and Uncoated Colored Silica Microparticles

Uncoated and coated colored microparticles encapsulating FD&C Yellow No. 5 were prepared according to the procedures described in Examples 1 and 2, respectively. The dye concentration in the resulting microparticles was 0.42% (wt/wt) and 90% of the microparticles were characterized by particles size smaller than 1.2 micron.

Example 17

Preparation of Modified Coated and Uncoated Colored Silica Microparticles

Uncoated and coated colored microparticles encapsulating a coloring agent such as, for example, FD&C Blue No. 1, FD&C Red No. 40 or FD&C Yellow No. 5, are prepared according to the procedures described in Examples 1 and 2, respectively, using a water-soluble siloxane monomer instead of TEOS in the Example 1. Examples of water-soluble siloxane monomers that are usable in this context are described, for example, in I. Gill, A. Ballesteros, J. Am. Chem. Soc. 120, 1998, 8587.

In this procedure, a clear, biphasic water-in-oil emulsion polymerization is performed upon adding to the acidic dye solution the siloxane monomer, the surfactants and the solvent.

Example 18

Preparation of Fluorescent Silica Microparticles

A mixture of the water-soluble fluorescent dye Rhodamine B (0.04 gram), tetraethylorthosilicate (TEOS, 30 grams) and a solution of 50% (wt/wt) acetic acid in water was stirred. The obtained solution was emulsified, by means of stirring under high-shear forces, in an oil phase containing 266 grams castor oil and 14 grams of a silicon based surfactant. The obtained emulsion was poured into 400 grams aliphatic alcohol (e.g., decanol) and the obtained mixture was stirred. A fine particulate powder was thus obtained, isolated and washes consecutively with an alcohol, until the alcoholic phase was clear. The typical fluorescence of the colored silica microparticles was clearly observed under UV-Vis radiation.

Example 19

Preparation of Fluorescent Silica Microparticles

Fluorescent silica microcapsules encapsulating Fluorescein were prepared as described in Example 18, using 0.04 grams Fluorescein instead of Rhodamine B. The typical fluorescence of the colored silica microparticles was clearly observed under UV-Vis radiation.

Example 20

Preparation of Fluorescent Silica Microparticles

Fluorescent silica microcapsules encapsulating Pyronine were prepared as described in Example 18, using 0.04 grams Pyronine instead of Rhodamine B. The typical fluorescence of the colored silica microparticles was clearly observed under UV-Vis radiation.

Example 21

Preparation of Coated Fluorescent Silica Microparticles 1-10 grams of any of the dry powders obtained in Examples 18-20 are suspended in 40 grams TEOS and the mixture is stirred at room temperature. 0.01-5N HCl (50-500 µl) is then added to the stirred dispersion. The obtained powder is separated as described hereinabove (in Example 1), and the precipitate is consecutively washed with hexane, ethanol, NaOH-containing ethanol, sodium lauryl sulfate solution (SLS), water and ethanol. The obtained particles are then dried in an oven.

Example 22

Compounding of Coated Colored Silica Microparticles in Polyethylene Beads

Figure 3:
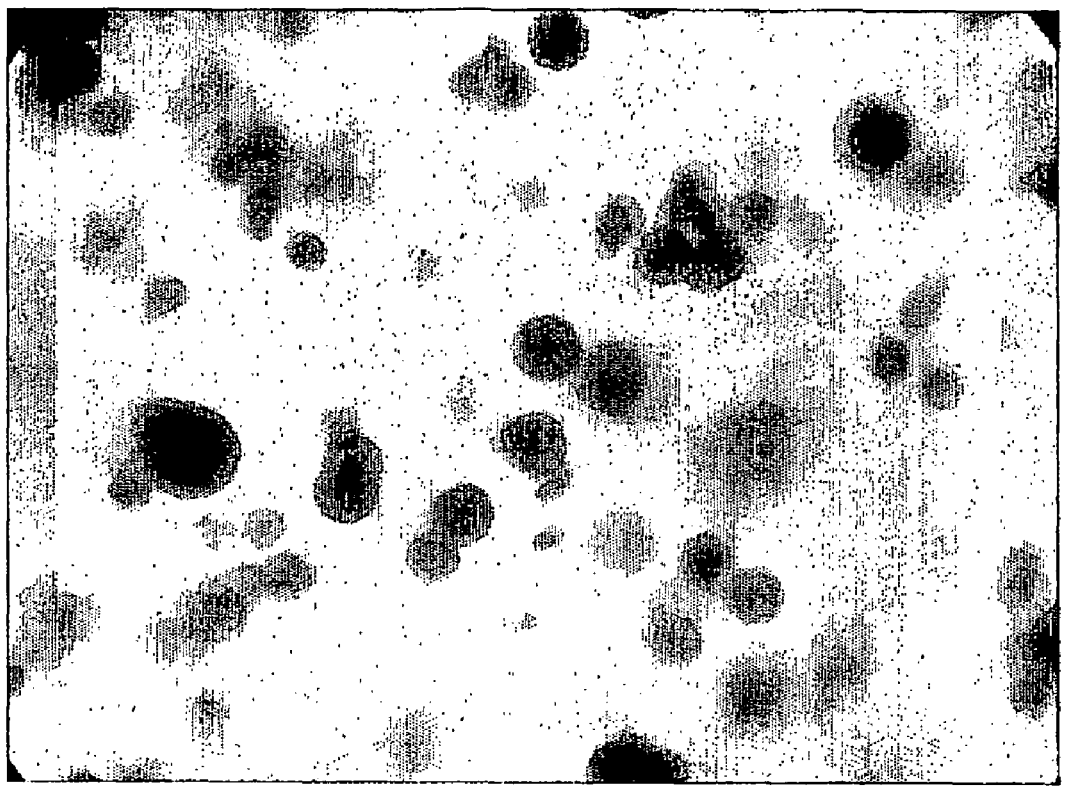
FIG. 3 presents an optical microscope picture of polyethylene beads that were compounded three times with colored (FD&C Blue 1) silica microspheres prepared according to a preferred embodiment of the present invention.

Coated colored microparticles encapsulating FD&C Blue No. 1 were prepared as described above and were compounded three times in polyethylene beads, using known techniques. As is shown in FIG. 3, no damage to both components, the beads and the particles, was observed in the compounded product.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of preparing substantially leachless, agent-encapsulating sol gel particles, the method comprising:
    emulsifying an inner phase containing at least one agent and at least one first sol-gel precursor in an outer phase containing a dispersing medium and producing initial sol-gel particles encapsulating said at least one agent; and
    reacting said initial sol-gel particles with at least one second sol-gel precursor, thereby obtaining said substantially leachless, agent-encapsulating sol-gel particles;
    wherein said substantially leachless agent-encapsulating sol-gel particles are characterized by leaching of no more than 2 weight percentages of said at least one agent from therein upon mixing and agitating said sol gel particles with an extraction medium for at least 7 days at 40° C.

2. The method of claim 1, wherein said agent is a colorant.

3. The method of claim 1, wherein an average particles size of said substantially leachless sol-gel particles ranges between 0.05 micron and 5 microns in diameter.

4. The method of claim 1, wherein a surface area of said substantially leachless sol-gel particles ranges between 0.01 $m^2$/gram and 5 $m^2$/gram.

5. The method of claim 1, wherein a concentration of said at least one agent ranges between 0.1 weight percentages and 20 weight percentages of said substantially leachless sol-gel particles.

6. The method of claim 1, wherein said inner phase further comprises a water miscible solvent.

7. The method of claim 1, wherein said inner phase further comprises at least one surfactant.

8. The method of claim 1, wherein said outer phase further comprises at least one oil miscible solvent.

9. The method of claim 1, wherein said outer phase further comprises at least one surfactant.

10. The method of claim 1, wherein said outer phase further comprises at least one viscosity modifying agent.

11. The method of claim 1, wherein said dispersing medium is a hydrophobic dispersing medium.

12. The method of claim 1, wherein said reacting is performed in the presence of a catalyst.

13. The method of claim 1, further comprising one or more of washing said initial or said substantially leachless sol-gel particles, with at least one solvent or of drying one of said initial or said substantially leachless sol-gel particles.

14. A method of preparing a colored cosmetic product stable to color leaching and/or migration, the method comprising:
    preparing substantially leachless particles by the method of claim 2; and
    mixing said substantially leachless colorant-encapsulating sol-gel particles with a cosmetic acceptable carrier.

15. A method of preparing a multicolored dentifrice composition stable to color bleeding, the method comprising:
    preparing a plurality of different colored dentifrice components being in physical interfacial contact therebetween at least one of said components containing substantially leachless, colorant-encapsulating sol-gel particles being prepared by
    the method of claim 2.

* * * * *